(12) United States Patent
Deng et al.

(10) Patent No.: US 9,980,936 B2
(45) Date of Patent: May 29, 2018

(54) BH4 ANTAGONISTS AND METHODS RELATED THERETO

(71) Applicants: Emory University, Atlanta, GA (US); The Board of Regents of the University of Texas System, Austin, TX (US)

(72) Inventors: Xingming Deng, Lilburn, GA (US); Jia Zhou, League City, TX (US); Chunyong Ding, Galveston, TX (US)

(73) Assignees: Emory University, Atlanta, GA (US); The Board of Regents of the University of Texas System, Austin, TX (US)

( * ) Notice: Subject to any disclaimer, the term of this patent is extended or adjusted under 35 U.S.C. 154(b) by 0 days. days.

(21) Appl. No.: 15/309,382

(22) PCT Filed: May 5, 2015

(86) PCT No.: PCT/US2015/029206
§ 371 (c)(1),
(2) Date: Nov. 7, 2016

(87) PCT Pub. No.: WO2015/171589
PCT Pub. Date: Nov. 12, 2015

(65) Prior Publication Data
US 2017/0071896 A1 Mar. 16, 2017

Related U.S. Application Data

(60) Provisional application No. 61/988,332, filed on May 5, 2014.

(51) Int. Cl.
*A61K 31/336* (2006.01)
*A61K 31/122* (2006.01)
*A61K 31/496* (2006.01)
*C07C 311/18* (2006.01)
*C07D 241/04* (2006.01)
*C07C 233/78* (2006.01)
*C07C 15/28* (2006.01)
*C07D 303/04* (2006.01)
*C07D 207/09* (2006.01)
*C07D 207/27* (2006.01)
*A61K 31/439* (2006.01)

(52) U.S. Cl.
CPC .......... *A61K 31/336* (2013.01); *A61K 31/122* (2013.01); *A61K 31/439* (2013.01); *A61K 31/496* (2013.01); *C07C 15/28* (2013.01); *C07C 233/78* (2013.01); *C07C 311/18* (2013.01); *C07D 207/09* (2013.01); *C07D 207/27* (2013.01); *C07D 241/04* (2013.01); *C07D 303/04* (2013.01); *C07C 2101/02* (2013.01); *C07C 2103/24* (2013.01)

(58) Field of Classification Search
CPC .................................................. A61K 31/336
See application file for complete search history.

(56) References Cited

U.S. PATENT DOCUMENTS

| | | |
|---|---|---|
| 4,975,459 A | 12/1990 | Mehta |
| 5,141,957 A | 8/1992 | Jiang |
| 5,344,841 A * | 9/1994 | Jiang ..................... C07C 225/34 514/459 |
| 5,436,243 A | 7/1995 | Sachs |
| 5,733,880 A | 3/1998 | Mincher |
| 6,465,522 B1 | 10/2002 | Potter |

FOREIGN PATENT DOCUMENTS

WO 1998025885 6/1998

OTHER PUBLICATIONS

Jiang et al. J. Med. Chem., 1992, vol. 35, No. 23, pp. 4259-4263.*
Takano et al. The Journal of Pharmacology and Experimental Therapeutics, 1994, vol. 271, pp. 1027-1033.*
Johnson et al. Bioorganic & Medicinal Chemistry, 1997, vol. 5, No. 8, pp. 1469-1479.*
Chen et al. Targeting Bcl2 in cancer, Oncoscience 2015, vol. 2, No. 10, 813-814.
Deng et al. BCL2-BH4 antagonist BDA-366 suppresses human myeloma growth, Oncotarget, vol. 7, No. 19, 27753-27763, 2016.
Giatromanolaki et al. Relation of hypoxia inducible factor 1α and 2α in operable non-small cell lung cancer to angiogenic/molecular profile of tumours and survival, British Journal of Cancer (2001) 85(6), 881-890.
Han et al. Small Molecule Bcl2 BH4 Antagonist for Lung Cancer Therapy, Cancer Cell. 2015, 27(6): 852-863.
Jiang et al. Novel Non-Cross Resistant Diaminoanthraquinones as Potential Chemotherapeutic Agents, J. Med. Chem., 1992, 35(23):4259-4263.
Johnson et al. Antitumor Agents CLXVII. Synthesis and Structure-Activity Correlations of the Cytotoxic Anthraquinone 1,4-Bis-(2,3-Epoxypropylamino)-9,10-Anthracenedione, and of Related Compounds, Bioorganic & Medicinal Chemistry, vol. 5, No. 8, pp. 1469-1479, 1997.
Li et al. Modulation of Bax and mTOR for Cancer Therapeutics, Cancer Res; 77(11); 3001-12, 2017.
Liu et al. Rapamycin Induces Bad Phosphorylation in Association with Its Resistance to Human Lung Cancer Cells, Mol Cancer Ther. 2012,11(1): 45-56.
Liu et al. BH4 domain of Bcl-2 as a novel target for cancer therapy, Drug Discovery Today, vol. 21, No. 6, pp. 989-996, 2016.
Pugh et al. Hypoxia and oxidative stress in breast cancer Hypoxia signalling pathways, Breast Cancer Res 2001, 3:313-317.

(Continued)

Primary Examiner — James D. Anderson
(74) Attorney, Agent, or Firm — Emory Patent Group

(57) ABSTRACT

The disclosure relates to BH4 inhibitors and therapeutic uses relates thereto. In certain embodiments, the disclosure relates to methods of treating or preventing cancer, such as lung cancer, comprising administering therapeutically effective amount of a pharmaceutical composition comprising a compound disclosed herein or pharmaceutically acceptable salt to a subject in need thereof.

3 Claims, 7 Drawing Sheets

(56) References Cited

OTHER PUBLICATIONS

Scarfo et al. Reprogramming cell death: BCL2 family inhibition in hematological malignancies, Immunology Letters 155 (2013) 36-39
Semenza et al. Involvement of Hypoxia-Inducible Factor 1 in Human Cancer, Internal Medicine 41 : 79-83, 2002.
Stefanska et al. Synthesis of Unsymmetrically Substituted 1,4-Bis[(aminoalkyl)amino]anthracene-9,l0-diones as Potential Antileukemic Agents,Journal of Medicinal Chemistry, 1989, vol. 32, No. 8, 1724-1728.
Takano et al. A Diaminoathroquinone inhibitor of Angiogenesis, J Pharmacol Exp Ther. 1994, 271(2):1027-33.
Venitt et al. Anthracene-9,10-diones as Potential Anticancer Agents: Bacterial Mutation Studies of Amido-Substituted Derivatives Reveal an Unexpected Lack of Mutagenicity, J. Met Chem. 1998, 41, 3748-3752.
Zhong et al. Overexpression of Hypoxia-inducible Factor 1alpha in Common Human Cancers and Their Metastases, Cancer Research 59, 5830-5835, 1999.
Zhong et al. Hypoxia-Inducible Factor 1a and 1b Proteins Share Common Signaling Pathways in Human Prostate Cancer Cells, Biochemical and Biophysical Research Communications 284, 352-356 (2001).

* cited by examiner

A1-8

A1: X = O, R¹ = Me; A2: X = O, R¹ = Ph
A3: X = O, R¹ = CH$_3$C(O); A4: X = O, R¹ = CH$_3$SO$_2$
A5: X = CH$_2$, R¹ = Me; A6: X = CH$_2$, R¹ = Ph
A7: X = CH$_2$, R¹ = CH$_3$C(O); A8: X = CH$_2$, R¹ = CH$_3$SO$_2$

B1-4

B1: X = O, R² = OH
B2: X = O, R² = Cl
B3: X = CH$_2$, R² = OH
B4: X = CH$_2$, R² = Cl

BDA2

C1-4

C1: X = O, R³ = C(O)Ph
C2: X = CH₂, R³ = C(O)Ph
C3: X = O, R³ = SO₂Ph
C4: X = CH₂, R³ = SO₂Ph

D1-8

D1: R⁴ = Me;  D2: R⁴ = i-Pr
D3: R⁴ = Ph;  D4: R⁴ = CH₃C(O)
D5: R⁴ = PhC(O);  D6: R⁴ = CH₃SO₂;
D7: R⁴ = PhSO₂;  D8: R⁴ = p-Me-C₆H₄SO₂

E1: $R^5$ = $CH_3C(O)$; E2: $R^5$ = PhC(O)
E3: $R^5$ = p-Me-$C_6H_4$C(O); E4: $R^5$ = $CH_3SO_2$
E5: $R^5$ = $PhSO_2$; E6: $R^5$ = p-Me-$C_6H_4SO_2$

F1: $R^6$ = H, $R^7$ = H
F2: $R^6$ = H, $R^7$ = Cl
F3: $R^6$ = OMe, $R^7$ = H
F4: $R^6$ = OMe, $R^7$ = Cl

BH4 ANTAGONISTS AND METHODS RELATED THERETO

CROSS-REFERENCE TO RELATED APPLICATIONS

This application is the National Stage of International Application Number PCT/US2015/029206 filed May 5, 2015, which claims the benefit of priority to U.S. Provisional Application No. 61/988,332 filed May 5, 2014. The entirety of each of these applications is hereby incorporated by reference for all purposes.

STATEMENT REGARDING FEDERALLY FUNDED RESEARCH

This invention was made with government support under Grants R01CA136534 and DA028821 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 11078US_ST25.txt. The text file is 1 KB, was created on Nov. 7, 2016, and is being submitted electronically via EFS-Web.

BACKGROUND

The overall survival for non-small cell lung cancer (NSCLC) is about 16%, whereas for SCLC, overall survival is 6%. Jemal et al., CA Cancer J. Clin., (2007), 57, 43-66. Overcoming resistance of lung cancer to either chemo-radiotherapy or epidermal growth factor receptor (EGFR) targeted therapy would provide to be a significant achievement. B-cell lymphoma 2 protein (Bcl-2) is a member of the Bcl-2 family of apoptosis regulator proteins. Bcl-2 is extensively expressed in various types of cancer, including lung cancer, leukemia, breast cancer, prostatic cancer, pancreatic cancer, head/neck cancer, etc. One major factor implicated in the resistance of cancer to chemotherapy is the overexpression of Bcl-2 and Bcl-2-like proteins. The BH4 domain of Bcl-2 has been demonstrated to be a required domain for Bcl-2's anti-apoptotic function, which is associated with increased chemo-resistance of cancers. Bcl-2 is extensively expressed in both SCLC and NSCLC cells.

EGFR has been identified as an important therapeutic target for the treatment of NSCLC because more than 60% of NSCLC patients express EGFR. EGFR inhibition by EGFR-tyrosine kinase inhibitors (TKIs) (i.e. erlotinib or gefitinib) represents a promising approach for lung cancer therapy. Unfortunately, patients who initially benefited from erlotinib therapy developed acquired resistance to erlotinib after 6-12 months. The mechanisms are not fully understood but may be associated with activation of EGFR-independent pathways, occurrence of additional EGFR gene mutations or loss of the target.

In addition to acting as an antiapoptotic protein, Bcl-2 can also promote tumor angiogenesis. Under hypoxia Bcl-2 promotes hypoxia-inducible factor-1 (HIF-1)-mediated vascular endothelial growth factor (VEGF) expression in melanoma and breast carcinoma. See Trisciuoglio et al., Cell Death and Differentiation (2011), 1-12. Mutations at the BH4 domain abrogate the ability of Bcl-2 to induce VEGF protein expression and transcriptional activity under hypoxia in human melanoma cells and other human tumor histotypes, such as colon, ovarian and lung carcinomas. BH4 peptide is sufficient to increase HIF-1α protein half-life impairing HIF-1α protein ubiquitination and enhance VEGF secretion in melanoma cells exposed to hypoxia.

HIF-1 alpha is overexpressed in many tumor types including colon, breast, gastric, lung, skin, ovarian, pancreatic, prostate, and renal carcinomas. See abstract of Zhong et al., Cancer Res., 1999, 59(22):5830 entitled "Overexpression of hypoxia-inducible factor 1alpha in common human cancers and their metastases." See also Semenza, Intern Med., 2002, 41(2):79-83 entitled "Involvement of hypoxia-inducible factor 1 in human cancer;" Zhong et al., Biochem Biophys Res Commun., 2001, 284(2):352-6 entitled "Hypoxia-inducible factor 1alpha and 1beta proteins share common signaling pathways in human prostate cancer cells;" Pugh et al., Breast Cancer Res., 2001, 3(5):313-7 entitled "Hypoxia and oxidative stress in breast cancer. Hypoxia signalling pathways;" and Giatromanolaki et al., Br J Cancer., 2001, 85(6):881-90 entitled "Relation of hypoxia inducible factor 1 alpha and 2 alpha in operable non-small cell lung cancer to angiogenic/molecular profile of tumours and survival."

Certain diaminoanthraquinone derivatives are angiogenesis inhibitors and have been proposed as potential anticancer drugs. See Takano et al., Journal of Pharmacology and Experimental Therapeutics, (1994), 271(2), 1027-33. See also U.S. Pat. Nos. 6,465,522, 5,733,880, 5,436,243, and 5,344,841.

SUMMARY

The disclosure relates to BH4 inhibitors and therapeutic uses relates thereto. In certain embodiments, the disclosure relates to methods of treating or preventing cancer, such as lung cancer, comprising administering therapeutically effective amount of a pharmaceutical composition comprising a compound disclosed herein or pharmaceutically acceptable salt to a subject in need thereof. In certain embodiments, the disclosure relates to compounds or derivatives disclosed herein optionally substituted with one or more substituents.

In certain embodiments, the disclosure relates to compounds of Formula I,

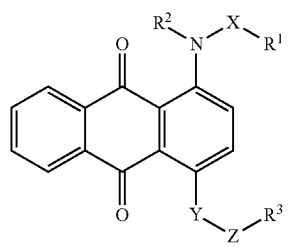

Formula I or salts thereof wherein X is $-(CR^8R^9)_n-$; Y is halogen, NH, CH$_2$, O, or S; Z is $-(CR^{10}R^{11})_m-$ or a bridging aryl group; n is 1, 2, 3, or 4; m is 1, 2, 3, or 4;

R$^1$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^{12}$;

$R^2$ is hydrogen or alkyl; or $R^1$ and $R^2$ form a heterocyclyl optionally substituted with one or more $R^{12}$;

$R^3$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^{12}$;

$R^8$, $R^9$, $R^{10}$, and $R^{11}$ are each individually and independently hydrogen, halogen, or hydroxy;

$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$;

$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to pharmaceutical compositions comprising compounds disclosed herein or pharmaceutically acceptable salts and a pharmaceutically acceptable excipient. In certain embodiments the pharmaceutical compositions further comprising a second therapeutic agent.

In certain embodiments, the disclosure relates to methods of treating or preventing cancer comprising administering a pharmaceutical composition disclosed herein to a subject diagnosed with, exhibiting symptoms of, or at risk of cancer. In certain embodiments, the cancer is selected from the group consisting of leukemia, melanoma, cervical, ovarian, colon, breast, gastric, lung, skin, ovarian, pancreatic, prostate, head, neck, and renal cancer. In certain embodiments, the pharmaceutical composition is administered in combination with a second chemotherapeutic agent such as, but not limited to, gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vincristine, vinblastine, vindesine, vinorelbine taxol, taxotere, etoposide, teniposide, amsacrine, topotecan, camptothecin, bortezomib, anegrilide, tamoxifen, toremifene, raloxifene, droloxifene, iodoxyfene fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, bevacizumab, combretastatin, thalidomide, and/or lenalidomide or combinations thereof.

In certain embodiments, the disclosure relates to therapeutic methods disclosed herein wherein the pharmaceutical compositions are administered before, after or during radiotherapy.

In certain embodiments, the disclosure relates to methods of treating lung cancer comprising administering an EGFR inhibitor in combination with a BH4 inhibitor, such as those disclosed herein.

In certain embodiments, the BH4 inhibitor is 1-((3-(diethylamino)-2-hydroxypropyl)amino)-4-((oxiran-2-ylmethyl)amino)anthracene-9,10-dione, 1,4-bis((oxiran-2-ylmethyl)amino)anthracene-9,10-dione, 1-((2-(dimethylamino)ethyl)amino)-4-((oxiran-2-ylmethyl)amino)anthracene-9,10-dione, 1-((2-hydroxy-3-(piperidin-1-yl)propyl)amino)-4-((oxiran-2-ylmethyl)amino)anthracene-9,10-dione, salts or derivatives thereof optionally administered at between 0.01 and 0.1 mg per kg daily, 0.1 and 1.0 mg per kg daily, 1 and 5 mg per kg daily, or 5 and 30 mg per kg of the subject daily.

In certain embodiments, the disclosure relates to methods of treating cancer comprising administering an effective amount of an mTOR inhibitor in combination with a BH4 inhibitor, such as those disclosed herein. In certain embodiments, the mTOR inhibitor is sirolimus, everolimus, ridaforolimus, temsirolimus, or derivatives thereof.

In certain embodiments, the disclosure relates to uses of compounds disclosed herein in the production of a medicament for the treatment or prevention of cancer.

In certain embodiments, the disclosure relates to methods of preparing compounds disclosed herein comprising mixing starting material and reagents disclosed herein under conditions that the compounds are formed.

DETAILED DESCRIPTION

Figure 1:
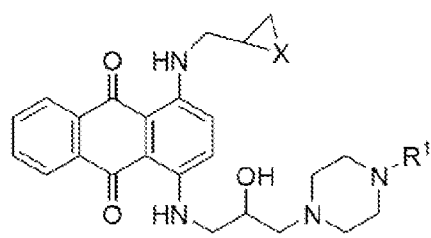
FIG. 1 illustrates the chemical structures of certain embodiments.
Figure 1:
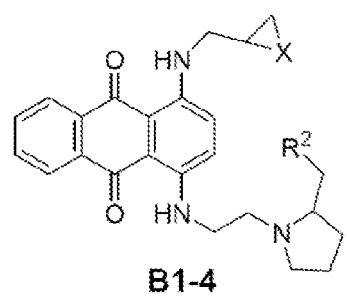
Figure 1:
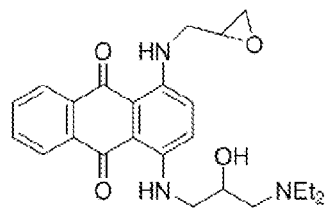
Figure 1:
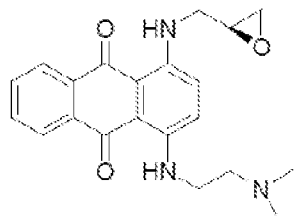
Figure 1:
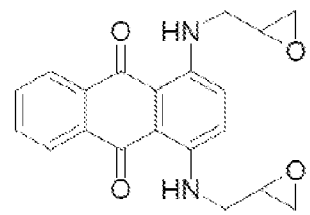
Figure 1:
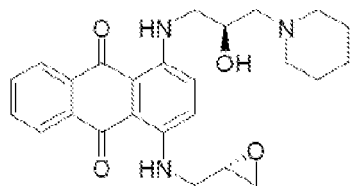

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of immunology, medicine, organic chemistry, biochemistry, molecular biology, pharmacology, physiology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

As used herein, "alkyl" means a noncyclic straight chain or branched, unsaturated or saturated hydrocarbon such as those containing from 1 to 10 carbon atoms, while the term "lower alkyl" or "$C_{1-4}$alkyl" has the same meaning as alkyl but contains from 1 to 4 carbon atoms. The term "higher alkyl" has the same meaning as alkyl but contains from 7 to 20 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butyryl, 2-butyryl, 1-pentynyl, 2-pentynyl, 3-methyl-1-butyryl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers to an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above with the indicated number of carbon atoms attached through a sulfur bridge. An example of an alkylthio is methylthio, (i.e., —S—CH3).

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers to an alkyl group as defined above with the indicated number of carbon atoms attached through an amino bridge. An example of an alkylamino is methylamino, (i.e., —NH—CH3).

"Alkanoyl" refers to an alkyl as defined above with the indicated number of carbon atoms attached through a carbonyl bride (i.e., —(C=O)alkyl).

"Alkylsulfonyl" refers to an alkyl as defined above with the indicated number of carbon atoms attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfonamide" refers to an alkyl as defined above with the indicated number of carbon atoms attached through a sulfamoyl bridge (i.e., —NHS(=O)$_2$alkyl), and an "Arylsulfonamide" refers to an alkyl attached through a sulfamoyl bridge (i.e., —NHS(=O)$_2$aryl).

"Alkylsulfinyl" refers to an alkyl as defined above with the indicated number of carbon atoms attached through a sulfinyl bridge (i.e. —S(=O)alkyl).

"Phosphinyl" refers to a phosphoryl (—P=O) or phosphothiol (—P=S) bridge having two additional substitutions of hydroxy, thiol, alkyl, alkoxy, alkylthio, or combinations (i.e., —P(=O)(alkyl)$_2$, —P(=S)(OH)$_2$, —P(=O)(alkyl)(alkoxy)).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO2Rb, —C(=O)Ra, —C(=O)ORa, —C(=O)NRaRb, —OC(=O)NRaRb, —ORa, —SRa, —SORa, —S(=O)2Ra, —OS(=O)2Ra and —S(=O)2ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing a oxygen atom with a sulfur atom or replacing a amino group with a hydroxyl group. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" can be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It can also be identified by a change in relevant biomarker or gene expression profile, such as PSA for prostate cancer, HER2 for breast cancer, or others.

Compounds

In certain embodiments, the disclosure contemplates compounds as provided for in Formula I below,

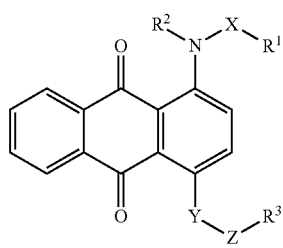

Formula I or salts thereof wherein
X is —(CR$^8$R$^9$)$_n$—;
Y is halogen, NH, CH$_2$, O, or S;
Z is —(CR$^{10}$R$^{11}$)$_m$— or a bridging aryl group;
n is 1, 2, 3, or 4;
m is 1, 2, 3, or 4;
R$^1$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^1$ is optionally substituted with one or more, the same or different, R$^{12}$;
R$^2$ is hydrogen or alkyl; or R$^1$ and R$^2$ form a heterocyclyl optionally substituted with one or more R$^{12}$;
R$^3$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^3$ is optionally substituted with one or more, the same or different, R$^{12}$;
R$^8$, R$^9$, R$^{10}$, and R$^{11}$ are each individually and independently hydrogen, halogen, or hydroxy;
R$^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{12}$ is optionally substituted with one or more, the same or different, R$^{13}$;
R$^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, R$^1$ is a carbocyclyl or heterocyclyl.

In certain embodiments, R$^1$ is cyclopropyl.

In certain embodiments, Y is NH or CH$_2$.

In certain embodiments, Y is halogen.

In certain embodiments, Z is —(CR$^{10}$R$^{11}$)$_m$—.

In certain embodiments, at least one of R$^{10}$ and R$^{11}$ is hydroxy.

In certain embodiments, m is 3.

In certain embodiments, R$^3$ is a carbocyclyl or heterocyclyl such as the heterocarbocycles oxiranyl, pyrrolidine, morpholinyl, pyrrolidone, and piperazinyl optionally substituted with one or more R$^{12}$.

In certain embodiments, R$^3$ is a heterocyclyl substituted with an alkyl, wherein the alkyl is substituted with one or more halogen or hydroxy.

In certain embodiments, R$^3$ is an alkylsulfonamide or arylsulfonamide optionally substituted with one or more R$^{12}$.

In certain embodiments, R$^3$ is dialkylamino.

In certain embodiments, R$^3$ is amino optionally substituted with one or more R$^{12}$.

In certain embodiments, R$^1$ is heterocyclyl.

In certain embodiments, n is 1 or 3.

In certain embodiments, Z is a bridging phenyl group.

In certain embodiments, the compounds of Formula I have Formula IA,

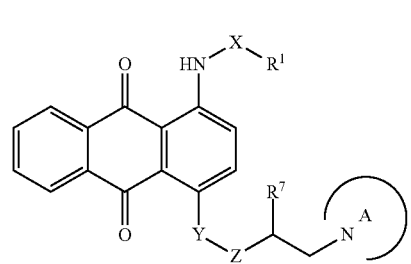

Formula IA or salts thereof wherein
A is a heterocyclic ring optionally substituted with one or more, R$^{12}$;
X is —(CR$^8$R$^9$)$_n$—;
Y is NH or CH$_2$;
Z is —(CR$^{10}$R$^{11}$)$_m$—;
n is 1, 2, 3, or 4;
m is 1, 2, 3, or 4;
R$^1$ is a hydroxy, carbocyclyl or heterocyclyl, wherein R$^1$ is optionally substituted with one or more, the same or different, R$^{12}$;
R$^7$ is hydrogen, halogen, or hydroxy;
R$^8$, R$^9$, R$^{10}$, and R$^{11}$ are each individually and independently hydrogen, halogen, or hydroxy;
R$^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{12}$ is optionally substituted with one or more, the same or different, R$^{13}$;
R$^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the compounds of Formula I have Formula IB,

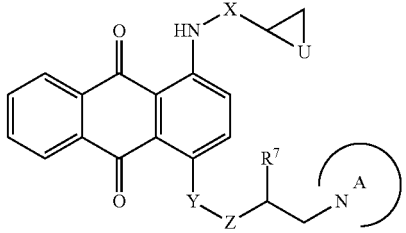

Formula IB or salts thereof wherein

A is a heterocyclic ring optionally substituted with one or more, $R^{12}$;

U is $CH_2$ or O;

X is —$(CR^8R^9)_n$—;

Y is NH or $CH_2$;

Z is —$(CR^{10}R^{11})_n$—;

n is 1, 2, 3, or 4;

m is 1, 2, 3, or 4;

$R^7$ is hydrogen, halogen, or hydroxy;

$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$;

$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the compounds of Formula I have Formula IC,

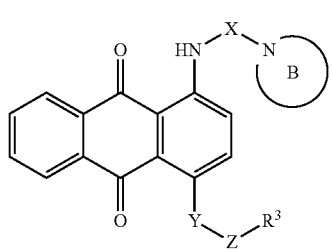

Formula IC or salts thereof wherein

B is a heterocyclic ring optionally substituted with one or more, $R^{12}$;

X is —$(CR^8R^9)_n$—;

Y is NH or $CH_2$;

Z is —$(CR^{10}R^{11})_m$— or a bridging aryl group;

n is 1, 2, 3, or 4;

m is 1, 2, 3, or 4;

$R^3$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^{12}$;

$R^8$, $R^9$, $R^{10}$, and $R^{11}$ are each individually and independently hydrogen, halogen, or hydroxy;

$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$;

$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the compound is selected from the group:

1-((cyclopropylmethyl)amino)-4-((3-morpholinopropyl)amino)anthracene-9,10-dione;

1-((3-morpholinopropyl)amino)-4-((3-(2-oxopyrrolidin-1-yl)propyl)amino)anthracene-9,10-dione;

1-((2,3-dihydroxypropyl)amino)-4-((3-morpholinopropyl)amino)anthracene-9,10-dione;

1-((2-(1-methylpyrrolidin-2-yl)ethyl)amino)-4-((3-morpholinopropyl)amino)anthracene-9,10-dione;

1-(3-hydroxyazetidin-1-yl)-4-((3-morpholinopropyl)amino)anthracene-9,10-dione;

1-((3-morpholinopropyl)amino)-4-((oxiran-2-ylmethyl)amino)anthracene-9,10-dione;

1-((2-((2-hydroxyethyl)amino)ethyl)amino)-4-((3-morpholinopropyl)amino)anthracene-9,10-dione;

1,4-bis((2-hydroxy-3-morpholinopropyl)amino)anthracene-9,10-dione;

1-((2-hydroxy-3-morpholinopropyl)amino)-4-((oxiran-2-ylmethyl)amino)anthracene-9,10-dione;

1-((3-(4-acetylpiperazin-1-yl)-2-hydroxypropyl)amino)-4-((oxiran-2-ylmethyl)amino)anthracene-9,10-dione;

1-((2-hydroxy-3-(piperidin-1-yl)propyl)amino)-4-((oxiran-2-ylmethyl)amino)anthracene-9,10-dione;

1-((2-(dimethylamino)ethyl)amino)-4-((oxiran-2-ylmethyl)amino)anthracene-9,10-dione;

1-((cyclopropylmethyl)amino)-4-((2-hydroxy-3-(piperidin-1-yl)propyl)amino) anthracene-9,10-dione;

1-((3-(4-acetylpiperazin-1-yl)-2-hydroxypropyl)amino)-4-(3-morpholinopropyl)amino) anthracene-9,10-dione;

1-((cyclopropylmethyl)amino)-4-((oxiran-2-ylmethyl)amino)anthracene-9,10-dione; and 1-((cyclopropylmethyl)amino)-4-((3-(diethylamino)-2-hydroxypropyl)amino)anthracene-9,10-dione or wherein the compound is optionally substituted with one or more substituent.

Small Molecule Bcl2 BH4 Antagonist for Lung Cancer Therapy

Bcl-2 is the founding member of the Bcl-2 family which suppresses apoptosis following various stresses. Mechanisms involved in inhibiting the survival function of Bcl-2 will promote cancer cells to undergo apoptosis. The Bcl-2 family members have homology clustered within four conserved Bcl-2 homology (BH) domains: BH1, BH2, BH3 and BH4, in which antiapoptotic proteins, such as Bcl-2, Bcl-XL, Bcl-w and A1, bear the NH2-terminal BH4 domain. This indicates that the BH4 domain represents a potential therapeutic target in light of its involvement in many cellular functions through the interactions with different proteins. BH4 domain-targeted agents (BDAs) suppress Bcl-2 and other Bcl-2-like proteins bearing the BH4 domain. Our findings indicate that most human lung cancer cell lines are more sensitive to BDA2 than ABT-737, a BH3 mimetic small-molecule inhibitor that binds with high affinity to Bcl-2 and Bcl-xL. In certain embodiments, the disclosure relates to the use of compounds disclosed herein to treat cancer and other malignancies expressing the BH4-containing Bcl-2 family proteins.

The BH4 domain is required for the survival activity of Bcl2, and removal of this domain can convert Bcl2 from a survival to a killer molecule, suggesting that the BH4 domain constitutes a promising structure-based target for the disruption of Bcl2's survival function or conversion of Bcl2 into a death molecule. A class of Bcl2 antagonist (e.g. BDA-2, re-named as BDA-366) have been identified that target the BH4 domain and are distinct from previous BH3 mimetics. BDA-366 directly binds to purified Bcl2 protein selectively at the BH4 domain with high affinity, with an inhibitory constant (Ki) value at the nanomolar level. BDA-366 failed to bind other Bcl2 family members (i.e. Bcl-XL, Mcl-1 and Bfl-1/A1), demonstrating the specificity of Bcl2/BDA-366 binding. The binding of BDA-366 with the BH4 domain resulted in Bcl2 conformational change and exposure of the BH3 domain in vitro and in vivo.

BDA-366 demonstrated potent antitumor activity in lung cancer xenografts derived from either a lung cancer cell line or a patient-derived SCLC tumor. Dose-response experiments revealed that doses of BDA-366 between 10 and 30 mg/kg/d potently suppress lung cancer growth in vivo without platelet reduction or other significant normal tissue toxicity, indicating that this dose range should be effective and safe in murine lung cancer models.

Since BDA-366 effectively suppressed the growth of PDX raised from a patient with refractory SCLC, there is a good possibility that BDA-366 may provide clinical utility in patients. Cancer cells overexpressing Bcl2 are resistant to mTOR inhibitor and down-regulation of Bcl2 restores sensitivity to mTOR inhibition. Inhibition of mTOR by RAD001 resulted in Bcl2 up-regulation in lung cancer cell lines and in tumor tissues from NSCLC patients treated with RAD001. It is possible that Bcl2 expression induced by mTOR inhibitor therapy may negatively affect the efficacy of mTOR inhibitor in lung therapy. This may help explain why RAD001 only had limited efficacy in lung cancer patients. Combined Bcl2 and mTOR inhibition should have superior therapeutic benefits over each agent alone. BDA-366 in combination with RAD001 exhibited strong synergistic activity against lung cancer in vitro and in vivo without significant normal tissue toxicity. Co-targeting Bcl2 and mTOR offers a more effective strategy for lung cancer treatment.

BDA-366 is a Bcl2 antagonist that selectively targets the BH4 domain of Bcl2. The binding of BDA-2 with the BH4 domain results in conversion of Bcl2 from an antiapoptotic molecule into a death protein through a conformational change that exposes its BH3 death domain. The BH4 antagonist BDA-366 exhibits potent efficacy against human lung cancer in vivo without platelet reduction. Development of the BH4 antagonist as an anti-cancer agent indicates a combination mTOR strategy for cancer therapeutics.

In certain embodiments, the mTOR inhibitor is sirolimus, everolimus, ridaforolimus, temsirolimus, or derivatives thereof. In certain embodiments, derivative are contemplated of the following formula,

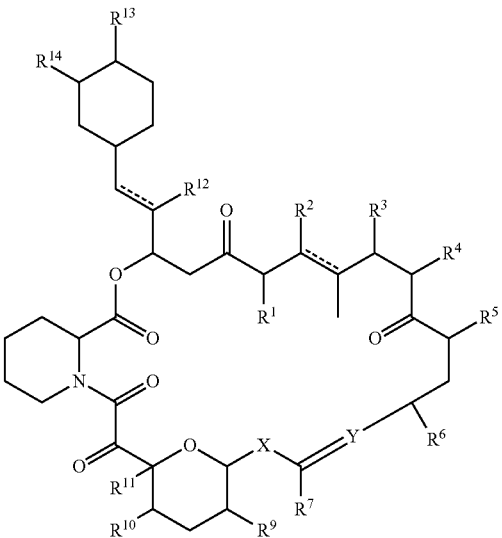

or salts thereof wherein, the dotted lines each individually represent a single or double bond;

Y is the bridging group =CH—CH=CH—CH=CH—;

X is —(CHR$^8$)$_n$—;

n is 1 or 2

R$^1$, R$^2$, R$^3$, R$^4$, R$^5$, R$^7$, R$^8$, R$^9$, R$^{10}$, R$^{11}$, R$^{12}$, R$^{13}$, and R$^{14}$ are each the same or different, individually and independently at each occurrence, hydrogen, alkyl, alkenyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, phosphinyl, carbocyclyl, aryl, or heterocyclyl, wherein each R$^1$, R$^2$, R$^3$, R$^4$, R$^5$, R$^7$, R$^8$, R$^9$, R$^{10}$, R$^{11}$, R$^{12}$, R$^{13}$, and R$^{14}$ are optionally substituted with one or more, the same or different, R$^{20}$;

R$^{20}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, phosphinyl, carbocyclyl, aryl, or heterocyclyl, wherein R$^{20}$ is optionally substituted with one or more, the same or different, R$^{21}$; and R$^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

It has been discovered that treatment of lung cancer cells with erlotinib results in up-regulation of Bcl-2/Bcl-XL, which may partially contribute to the resistance of lung cancer to erlotinib. A combined EGFR and Bcl-2 inhibition may overcome the erlotinib resistance. Treatment of lung cancer cells with a combination of BDA-366 and erlotinib synergistically induces apoptosis and augments growth inhibition. This disclosure contemplates that a combined EGFR and Bcl-2 inhibition is a strategy for overcoming erlotinib resistance and improving prognosis of lung cancer.

Combination Therapies

The cancer treatments disclosed herein can be applied as a sole therapy or can involve, conventional surgery or radiotherapy or chemotherapy. Such chemotherapy can include one or more of the following categories of anti-tumor agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulfan and nitrosoureas); antimetabolites (for example antifolates such as fluoropyrimidines like 5-fluorouracil and gemcitabine, tegafur, raltitrexed, methotrexate, cytosine arabinoside and hydroxyurea); antitumor antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin); and proteosome inhibitors (for example bortezomib [Velcade®]); and the agent anegrilide [Agrylin®]; and the agent alpha-interferon (ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-Her2 antibody trastuzumab and the anti-epidermal growth factor receptor (EGFR) antibody, cetuximab), farnesyl transferase inhibitors, tyrosine kinase inhibitors and serine/threonine kinase inhibitors, for example inhibitors of the epidermal growth factor family for example EGFR family tyrosine kinase inhibitors such as: N-(3-chloro-4-fluorophenyl)-7-methoxy-6-(3-morpholinopropoxy)quinazolin-4-amine (gefitinib), N-(3-ethynylphenyl)-6,7-bis(2-methoxyethoxy)quinazolin-4-amine (erlotinib), and 6-acrylamido-N-(3-chloro-4-fluorophenyl)-7-(3-morpholinopropoxy)quinazolin-4-amine (CI 1033), for example inhibitors of the platelet-derived growth factor family and for example inhibitors of the hepatocyte growth factor family, for example inhibitors of phosphotidylinositol 3-kinase (PI3K) and for example inhibitors of mitogen activated protein kinase kinase (MEK1/2) and for example inhibitors of protein kinase B (PKB/Akt), for example inhibitors of Src tyrosine kinase family and/or Abelson (Abl) tyrosine kinase family such as dasatinib (BMS-354825) and imatinib mesylate (Gleevec™); and any agents that modify STAT signalling;

(v) antiangiogenic agents such as those which inhibit the effects of vascular endothelial growth factor, (for example the anti-vascular endothelial cell growth factor antibody bevacizumab [Avastin™]) and compounds that work by other mechanisms (for example linomide, inhibitors of integrin ocvβ3 function and angiostatin);

(vi) vascular damaging agents such as Combretastatin A4;

(vii) antisense therapies, for example those which are directed to the targets listed above, such as an anti-RAS antisense; and (viii) immunotherapy approaches, including for example ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumor cell lines and approaches using anti-idiotypic antibodies, and approaches using the immunomodulatory drugs thalidomide and lenalidomide [Revlimid®].

Formulations

Pharmaceutical compositions disclosed herein can be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure can also form internal salts, and such compounds are within the scope of the disclosure. When a compound contains a hydrogen-donating heteroatom (e.g. NH), salts are contemplated to cover isomers formed by transfer of the hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases can also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein can be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Examples of structuring a compound as prodrugs can be found in the book of Testa and Caner, Hydrolysis in Drug and Prodrug Metabolism, Wiley (2006) hereby incorporated by reference. Typical prodrugs form the active metabolite by transformation of the prodrug by hydrolytic enzymes, the hydrolysis of amides, lactams, peptides, carboxylic acid esters, epoxides or the cleavage of esters of inorganic acids.

Pharmaceutical compositions typically comprise an effective amount of a compound and a suitable pharmaceutical acceptable carrier. The preparations can be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is made to U.S. Pat. Nos. 6,372,778, 6,369,086 6,369,087 and U.S. Pat. No. 6,372,733 and the further references mentioned above, as well as to the standard handbooks, such as the latest edition of Remington's Pharmaceutical Sciences. It is well known that ester prodrugs are readily degraded in the body to release the corresponding alcohol. See e.g., Imai, Drug Metab Pharmacokinet (2006) 21(3):173-85, entitled "Human carboxylesterase isozymes: catalytic properties and rational drug design."

Generally, for pharmaceutical use, the compounds can be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and can be suitably packaged, for example in a box, blister, vial, bottle, sachet, ampoule or in any other suitable single-dose or multi-dose holder or container (which can be properly labeled); optionally with one or more leaflets containing product information and/or instructions for use. Generally, such unit dosages will contain between 1 and 1000 mg, and usually between 5 and 500 mg, of the at least one compound of the disclosure e.g., about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount," by which it is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which can be administered as a single daily dose, divided over one or more daily doses. The amount(s) to be administered, the route of administration and the further treatment regimen can be determined by the treating clinician, depending on factors such as the age, gender and general condition of the patient and the nature and severity of the disease/symptoms to be treated. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Formulations containing one or more of the compounds described herein can be prepared using a pharmaceutically acceptable carrier composed of materials that are considered safe and effective and can be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which can include plasticizers, pigments, colorants, stabilizing agents, and glidants. Delayed release, extended release, and/or pulsatile release dosage formulations can be prepared as described in standard references such as "Pharmaceutical dosage form tablets," eds. Liberman et. al. (New York, Marcel Dekker, Inc., 1989), "Remington—The science and practice of pharmacy," 20th ed., Lippincott Williams & Wilkins, Baltimore, Md., 2000, and "Pharmaceutical dosage forms and drug delivery systems," 6th Edition, Ansel et al., (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material can contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants can be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads, granules, or particles can also contain minor amount of nontoxic auxiliary substances such as wetting or emulsifying agents, dyes, pH buffering agents, or preservatives.

The compositions described herein can be formulation for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS can be mixed together in any desired ratio in order to ultimately obtain a sustained-release formulation having a desirable dissolution profile. Desirable sustained-release multiparticulate systems can be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers can also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition can be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and can be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials can also be used. Multi-layer coatings using different polymers can also be applied.

The preferred coating weights for particular coating materials can be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition can include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates can also be used. Pigments such as titanium dioxide can also be used. Small quantities of an anti-foaming agent, such as a silicone (e.g., simethicone), can also be added to the coating composition.

Alternatively, each dosage unit in the capsule can comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that can or can not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles can be formulated to provide immediate release, beads and granules are generally employed to provide delayed release.

EXPERIMENTAL

Analysis of Binding Affinity of BH4 Domain Antagonists (BDAs) to Bcl2 Protein In Vitro Using a Competitive Fluorescence Polarization Assay The principle of the fluorescence polarization assay is based on the observation that when a relatively small, fast-tumbling fluorescein-labeled peptide is excited with plane-polarized light, the emitted light is random with respect to the plane of polarization, resulting in a lower millipolarization (mP) value. Once a peptide binding to a bigger molecule (in this case, Bcl2), the complex tumbles much slower and the emitted light is polarized, resulting in a higher mP value. Thus, the change of mP reflects the interaction between the fluorescent-labeled peptide and the Bcl2 protein. Data (i.e. mP value) can be imported into Prism 3.0 to determine the dissociation constant ($K_d$) and the binding range for each peptide. The BH4 domain of Bcl2 directly interacts with c-Myc at its MBII domain.

A FITC-labeled peptide, QDCMWSGFSA (SEQ ID NO: 1), derived from the Bcl2 binding domain of c-Myc, was found to bind to the Bcl2 protein with high affinity ($K_d$: 19.32±2.86 nM). This interaction between Bcl2 and the peptide forms the basis for the fluorescence polarization assay. To measure the binding affinity of BDAs to Bcl2 protein, a competition fluorescence polarization assay was employed as described or as appropriately modified in Wang et al., Proc. Natl. Acad. Sci. USA, (2000), 97, 7124-7129; Zhang et al., Anal. Biochem., (2002), 307, 70-75; and Bruncko et al., J. Med. Chem., (2007), 50, 641-662, all hereby incorporated by reference.

The FITC-QDCMWSGFSA peptide (3 nM) was incubated with purified, human Bcl2 protein (6 nM) in the absence or presence of increasing concentrations (i.e. 0.1 nM~1 µM) of BDAs under standard buffer conditions in a 96-well assay plate. The plate was mixed on a shaker for 1 min and incubated at room temperature for an additional 15 min. The polarization, as defined as mP units, was measured at room temperature with a fluorescence microplate reader (Wallace, Calif.). A negative control (DMSO, 3 nM peptide and assay buffer) and a positive control (DMSO, 3 nM peptide, 6 nM Bcl2 and assay buffer) were used to determine the range of the assay. The percentage of inhibition was determined by (1−[(mP value of well−negative control)/range)]×100% Inhibitory constant (Ki) value was calculated using Microsoft Excel Results show that BDAs bind to Bcl2 protein with high affinity (BDA1: Ki=0.89±0.07 nM; BDA2: Ki=0.93±0.08 nM; BDA3: Ki=1.22±0.12 nM; BDA4: Ki=1.31±0.10 nM).

Synthetic Methods.

Compounds A1-8 (FIG. 1) may be synthesized as outlined in Scheme 1. Reaction of the commercially available 1,4-diamino-9,10-anthracinedione (1) with epichlorohydrin in glacial acetic acid will give rise to the bis-chlorohydrin 2 (Jiang et al., J. Med. Chem., (1992), 35, 4259-4263 hereby incorporated by reference). Treatment of 2 with piperazine intermediates in the presence of Et$_3$N will generate the quinone chlorohydrin 3. Ring closure of 3 in the presence of base will result in A1-4 in a similar fashion to the synthesis of compound BDA2. Mono-Boc-protection of one amino group of starting material 1 following the reported protocol (Bonger et al., ChemMedChem, 2009, 4, 2098-2102, hereby incorporated by reference) will produce the intermediate 4. Subsequent alkylation of 4 with (bromomethyl)cyclopropane will provide 5, followed by the Boc-deprotection upon the treatment with TFA. The remaining steps to generate compounds A5-8 are analogous to those leading to A1-4.

1,4-Bis(((S)-oxiran-2-ylmethyl)amino)anthracene-9,10-dione (CYD-2-84)

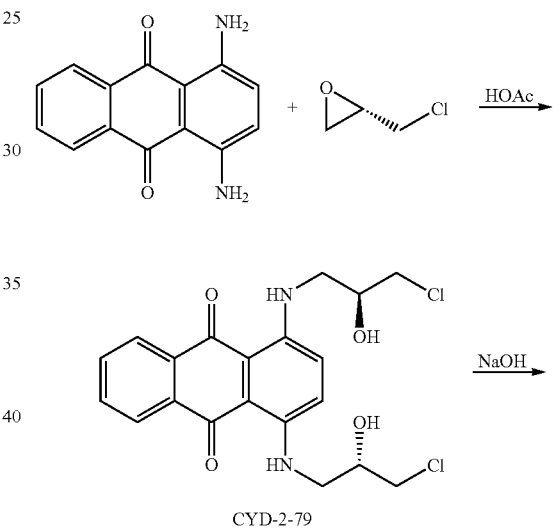

Scheme 1. Synthesis of Compounds A1-8.

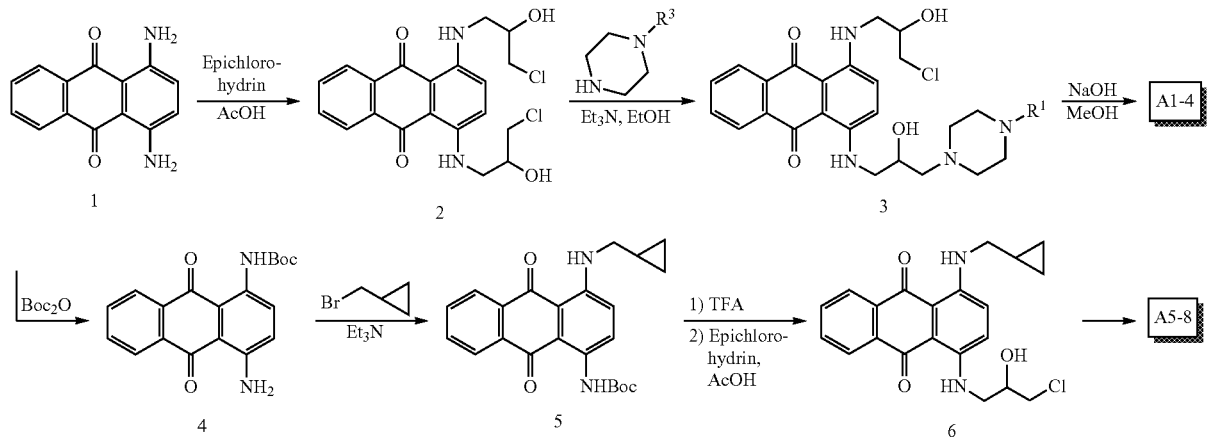

-continued

CYD-2-84

To a solution of 1,4-diaminoanthraquione (500 mg, 2.09 mmol) in glacial acetic acid (10 mL) at 70° C. was added (S)-epichlorohydrin (194.0 mg, 20.98 mmol) all at once. The reaction mixture was stirred at 75° C. for 2 hrs, and the volatiles were removed in vacuo. The resulting mixture was further purified by open column chromatography ($CH_2Cl_2$ with a methanol gradient of up to 2%) to provide a blue solid of the desired compound CYD-2-79 (480 mg, 54%). $^1H$ NMR (300 MHz, DMSO) δ 10.95 (t, J=5.6 Hz, 2H), 8.25 (dd, J=5.8, 3.3 Hz, 2H), 7.80 (dd, J=5.8, 3.5 Hz, 2H), 7.52 (s, 2H), 5.71 (d, J=4.2 Hz, 3H), 3.78-3.57 (m, 10H). $^{13}C$ NMR (75 MHz, DMSO) δ 181.29, 181.29, 146.54, 146.54, 134.30, 134.30, 132.85, 132.85, 126.20, 126.20, 125.12, 125.12, 109.12, 109.12, 69.79, 69.79, 47.77, 47.77, 45.91, 45.91.

To a solution of CYD-2-79 (226 mg, 0.52 mmol) in 1,4-dioxane (10 mL) was added a solution of KOH in EtOH (6 mL, 0.5 M). After stirring at rt for 15 min, TLC analysis showed that the starting material disappeared. The reaction mixture was diluted with dichloromethane (40 mL), washed with water (20 mL) and dried with anhydrous $Na_2SO_4$. The solvent was removed in vacuo, and the resulting residue was purified with a silica gel column; elution with $CH_2Cl_2$/MeOH=80:1 provided the desired product CYD-2-84 (130 mg, 69%) as a blue solid. $^1H$ NMR (300 MHz, $CDCl_3$) δ 10.79 (s, 2H), 8.36 (dd, J=5.9, 3.4 Hz, 2H), 7.73 (dd, J=5.8, 3.3 Hz, 2H), 7.36 (s, 2H), 3.80 (m, 2H), 3.60 (m, 2H), 3.28 (m, 2H), 2.88 (m, 2H), 2.75 (m, 2H). $^{13}C$ NMR (75 MHz, $CDCl_3$) δ 183.19, 183.19, 146.21, 146.21, 134.38, 134.38, 132.38, 132.38, 126.18, 126.18, 123.63, 123.63, 110.51, 110.51, 51.27, 51.27, 45.04, 45.04, 44.02, 44.02.

Scheme 2. Synthesis of Compounds B1-4 and C1-4.

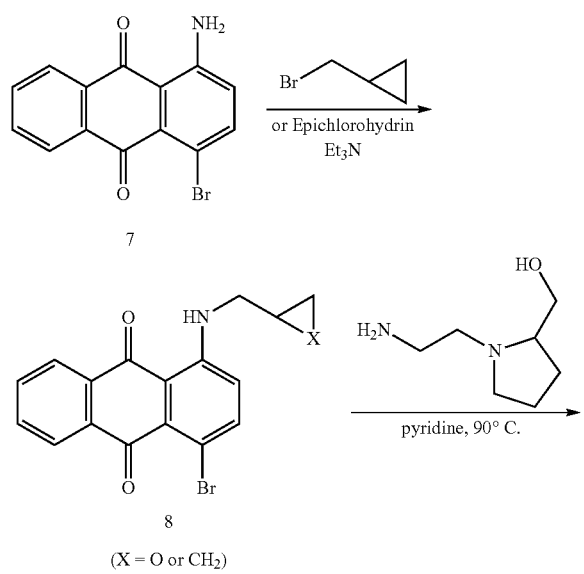

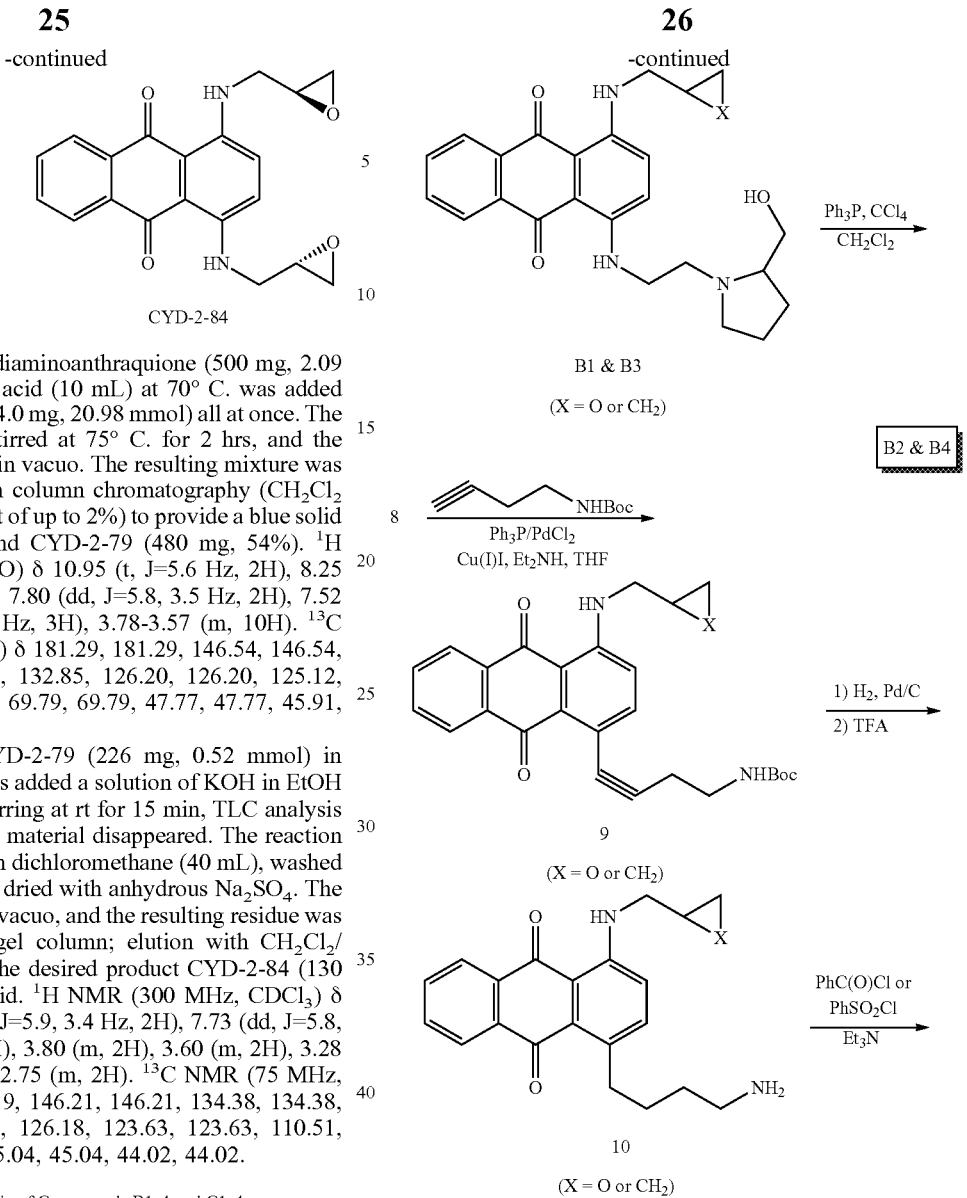

The synthesis of compounds B1-4 and C1-4 is depicted in Scheme 2. Key intermediate 8 will be prepared from the commercially available 1-amino-4-bromo-anthraquinone (7) by the alkylation with (bromomethyl)cyclopropane or epichlorohydrin in the presence of $Et_3N$. Reaction of 7 with 1-(2-aminoethyl)pyrrolidine, which can be prepared following the reported procedures (Pors el al., Med. Chem., 2005, 48, 6690-6695 and Pors et al., WO 2008/062252, both hereby incorporated by reference), in the presence of pyridine will provide the desired compounds B1 and B3. Chlorination of B1 and B3 with triphenylphosphinecarbon tetrachloride, a commonly employed complex reagent for conversion of alcohols to corresponding halides, will afford the target molecules B2 and B4. The Sonogashira coupling of 8 with N-Boc-protected butynylamine (Hirsh et al., J. Med. Chem., 2006, 49, 4098-4115) followed by the reduction of the triple bond and Boc-deprotection with TFA will afford the key intermediate 10. The subsequent treatment of 10 with appropriate acyl chlorides or sulfonyl chlorides in the presence of $Et_3N$ will generate target molecules C1-4.

Scheme 3. Synthesis of Compounds D1-8.

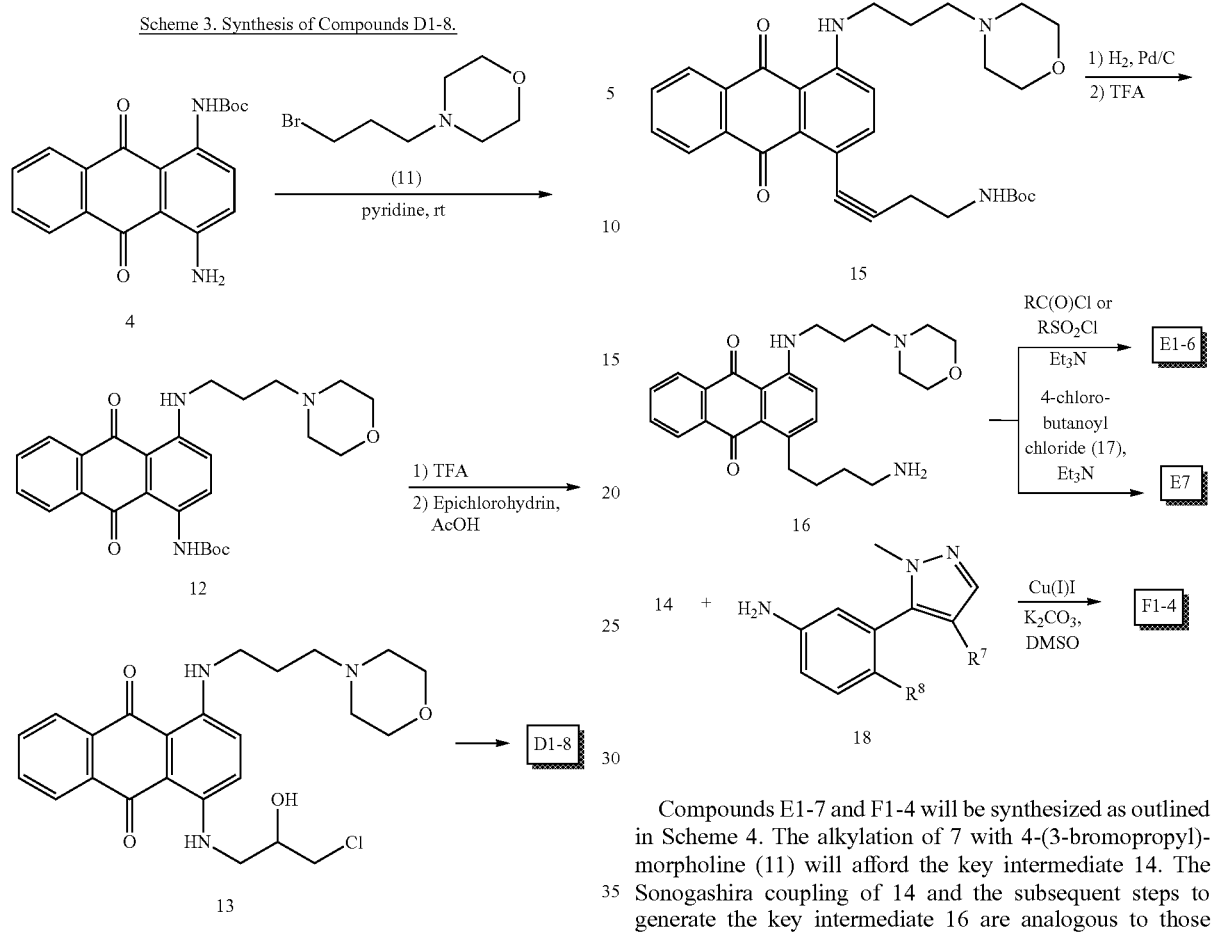

As outlined in Scheme 3, the alkylation of intermediate 4 with 4-(3-bromopropyl)-morpholine (11) in the presence of pyridine will afford intermediate 12. The Boc-deprotection of 12 and the remaining steps to generate compounds D1-8 are analogous to those leading to A5-8.

Scheme 4. Synthesis of Compounds E1-7 and F1-4.

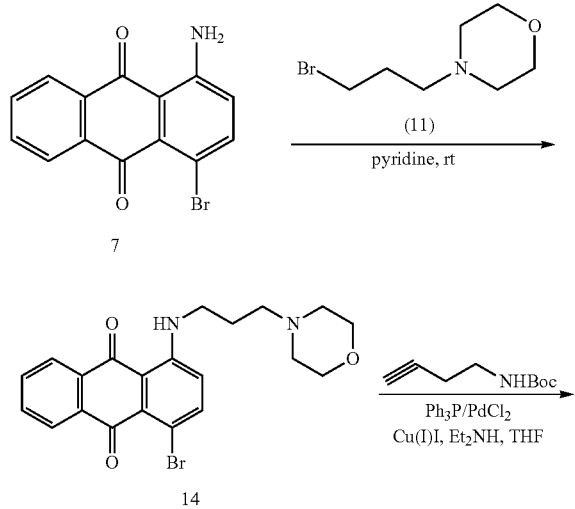

Compounds E1-7 and F1-4 will be synthesized as outlined in Scheme 4. The alkylation of 7 with 4-(3-bromopropyl)-morpholine (11) will afford the key intermediate 14. The Sonogashira coupling of 14 and the subsequent steps to generate the key intermediate 16 are analogous to those leading to 10. The treatment of 16 with appropriate acyl chlorides or sulfonyl chlorides will produce target molecules E1-6. Reaction of 16 with 4-chlorobutanoyl chloride (17) in the presence of $Et_3N$ (Ward et al., J. Med. Chem., 2010, 53, 5801-5812 hereby incorporated by reference) will result in E7. Intermediate 18 will be prepared according to Teegarden et al., J. Med. Chem., 2010, 53, 1923-1936 hereby incorporated by reference. Coupling of 14 with 18 in the presence of copper (I) iodide and potassium carbonate (Bradley et al., WO 2007/107539 hereby incorporated by reference) will afford the target molecules F1-4.

1-Fluoro-4-(3-morpholin-4-yl-propylamino)-anthraquinone

To a solution of 1, 4-difluoroanthraquione (500 mg, 2.04 mmol) in anhydrous DMSO (6 mL) was added 3-morpholinopropylamine (590 mg, 4.09 mmol) under nitrogen atmosphere. The resulting mixture was stirred at room temperature for 2 hrs. Then the reaction was monitored by TLC with ethyl acetate, indicating that the starting material disappeared. The reaction mixture was quenched with water (10 mL), and extracted with ethyl acetate (20 mL) for three times. The combined organic phases were washed with brine, and dried with anhydrous $Na_2SO_4$. The solvent was removed under vacuum to give a red residue, which was purified with silica gel column; eluting with ethyl acetate afforded the desired compound (600 mg, 80%) as a red solid. $^1$H-NMR (600 MHz, $CDCl_3$) δ 9.93 (s, 1H), 8.20 (d, 2H, J=7.8 Hz), 7.71 (m, 2H), 7.27 (m, 1H), 7.08 (m, 1H), 3.75 (t, 4H, J=4.2 Hz), 3.37 (m, 2H), 2.49 (m, 6H), 1.90 (m, 2H).

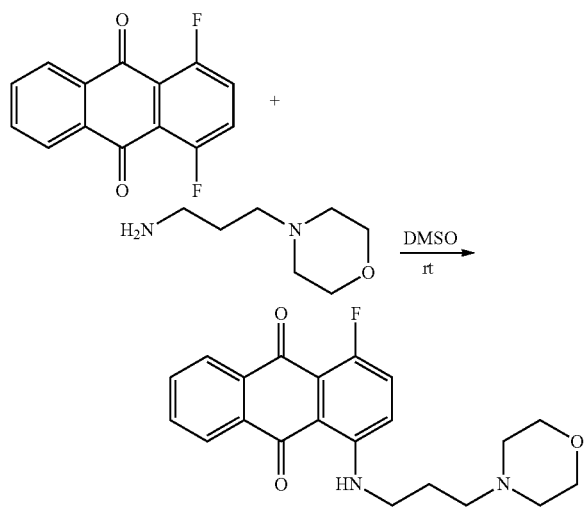

1-(2-Hydroxy-ethylamino)-4-(3-morpholin-4-yl-propylamino)anthraquinone (CYD-2-39)

To a solution of 1-fluoro-4-(3-morpholin-4-yl-propylamino)anthraquinone (132.0 mg, 0.35 mmol) in anhydrous DMSO (6 mL) was added ethanol amine (43.0 mg, 0.72 mmol). The resulting mixture was heated at 110° C. for 1 hr, and the color of reaction mixture turned into blue from red. Then the reaction was monitored by TLC, indicating that the starting material completely disappeared. The reaction mixture was quenched with water (10 mL), and extracted with ethyl acetate (20 mL) for three times. The combined organic phases were washed with brine, and dried with anhydrous $Na_2SO_4$. The solvent was removed under vacuum to give a blue residue, which was purified with silica gel column; eluting with $CH_2Cl_2$/MeOH=40:1 afforded the desired product (105 mg, 72%) as a blue foam. $^1$H-NMR (600 MHz, $CDCl_3$) δ 10.81 (s, 1H), 10.65 (s, 1H), 8.22 (m, 2H), 7.62 (m, 2H), 7.05 (d, 1H, J=9.6 Hz), 6.96 (d, 1H, J=9.6 Hz), 3.94 (m, 2H), 3.74 (m, 4H), 3.52 (d, 2H, J=4.8 Hz), 3.34 (m, 2H), 2.49 (m, 6H), 1.89 (t, 2H, J=7.2 Hz). $^{13}$C-NMR (150 MHz, $CDCl_3$) δ 182.2, 181.9, 146.3, 146.2, 134.5, 134.4, 131.9, 131.8, 126.0 (2C), 123.3 (2C), 110.1, 109.6, 67.0, 61.9, 56.3, 53.9, 45.2, 40.9, 26.7.

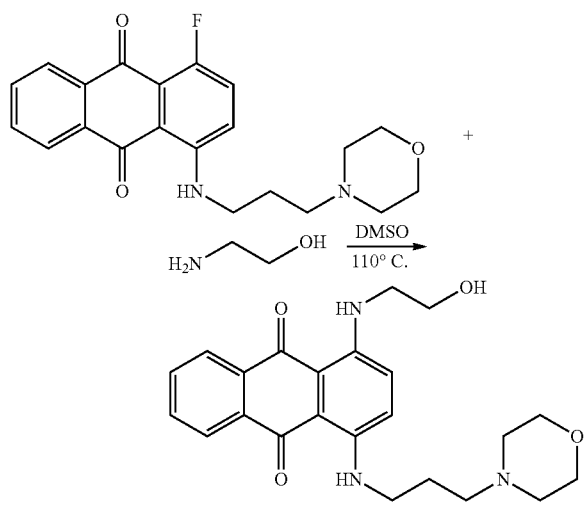

1-(Cyclopropylmethyl-amino)-4-(3-morpholin-4-yl-propylamino)anthraquinone (CYD-2-48)

To a solution of 1-fluoro-4-(3-morpholin-4-yl-propylamino)-anthraquinone (160.0 mg, 0.43 mmol) in anhydrous DMSO (6 mL) was added C-cyclopropyl-methylamine (62.0 mg, 0.87 mmol). The resulting mixture was heated at 110° C. for 3 hrs, and the reaction mixture turned into blue from red. Then the reaction was monitored by TLC, indicating that the starting material disappeared. The reaction mixture was quenched with water (10 mL), and extracted with ethyl acetate (20 mL) for three times. The combined organic phases were washed with brine, and dried with anhydrous $Na_2SO_4$. The removal of the solvent under vacuum gave a blue residue, which was purified with silica gel column; eluting with EtOAc/MeOH=60:1 afforded the desired product CYD-2-48 (110 mg, 60%) as a blue foam. $^1$H-NMR (600 MHz, $CDCl_3$) δ 10.7 (m, 2H), 8.29 (m, 2H), 7.64 (dd, 2H, J=3.0 Hz and 6.0 Hz), 7.16 (d, 1H, J=9.6 Hz), 7.09 (d, 1H, J=10.2 Hz), 3.69 (t, 4H, J=4.2 Hz), 3.39 (m, 2H), 3.20 (m, 2H), 2.44 (m, 6H), 1.86 (m, 2H), 1.20 (m, 1H), 0.61 (m, 2H), 0.30 (m, 2H). $^{13}$C-NMR (150 MHz, $CDCl_3$) δ 182.1 (2C), 146.0, 145.9, 134.4 (2C), 131.8 (2C), 125.9 (2C), 123.4 (2C), 109.7, 109.6, 66.9, 56.1, 53.7 (3C), 47.6, 40.7, 26.6, 10.8, 3.7 (2C).

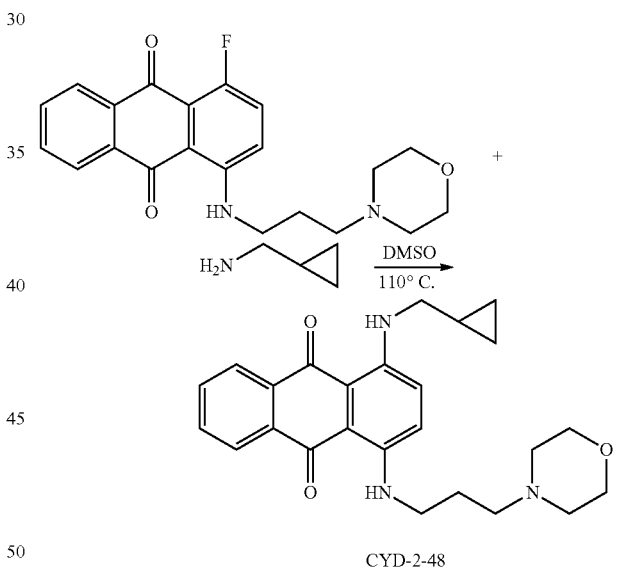

CYD-2-48

1-(3-Morpholin-4-yl-propylamino)-4-[3-(2-oxo-pyrrolidin-1-yl)-propylamino]-anthraquinone (CYD-2-45)

To a solution of 1-fluoro-4-(3-morpholin-4-yl-propylamino)anthraquinone (160.0 mg, 0.43 mmol) in anhydrous DMSO (6 mL) was added N-(3-aminopropyl)-2-pyrrolidinone (128.2 mg, 0.90 mmol). After stirring at 110° C. for 5 hrs, analysis of reaction mixture by TLC showed that starting material disappeared. The reaction mixture was quenched with water (10 mL), and extracted with ethyl acetate (20 mL) for three times. The combined organic phases were washed with brine, and dried with anhydrous Na₂SO₄. The removal of the solvent under vacuum led to a blue residue, which was purified with silica gel column; eluting with CH₂Cl₂/MeOH=60:1 afforded the desired compound CYD-2-45 (130 mg, 61%) as a blue foam. ¹H-NMR (600 MHz, CDCl₃) δ 10.75 (m, 2H), 8.31 (m, 2H), 7.67 (m, 2H), 7.22 (d, 1H, J=10.2 Hz), 7.15 (d, 1H, J=10.2 Hz), 3.73 (t, 4H, J=4.2 Hz), 3.42 (m, 8H), 2.49 (m, 6H), 2.38 (t, 2H, J=8.4 Hz), 2.0 (m, 4H), 1.91 (m, 2H). ¹³C-NMR (150 MHz, CDCl₃) δ 182.3, 182.1, 175.2, 146.1, 145.7, 134.4, 134.3, 131.9 (2C), 125.9, 123.5, 123.2, 109.8, 109.7, 66.9, 56.1, 53.7 (3C), 47.3, 40.7, 40.6 (2C), 30.9, 27.6, 26.6, 17.9.

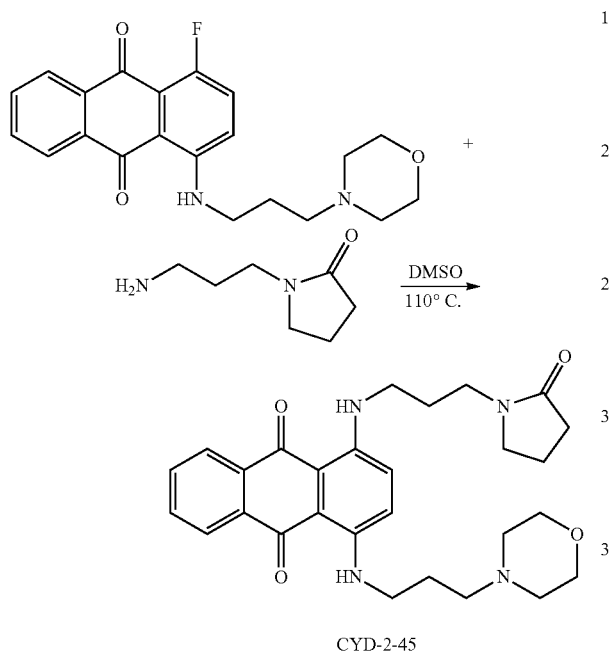

CYD-2-45

1-(2, 3-Dihydroxy-propylamino)-4-(3-morpholin-4-yl-propylamino)anthraquinone (CYD-2-49)

To a solution of 1-fluoro-4-(3-morpholin-4-yl-propylamino)anthraquinone (160.0 mg, 0.43 mmol) in anhydrous DMSO (6 mL) was added (±)-3-amino-1, 2-propanediol (79.7 mg, 0.87 mmol). After stirring at 110° C. for 3.5 hrs, analysis of reaction mixture by TLC demonstrated that the starting material was gone. The reaction mixture was quenched with water (10 mL), and extracted with ethyl acetate (20 mL) for three times. The combined organic phases were washed with brine, and dried with anhydrous Na₂SO₄. The solvent was removed under vacuum to generate a blue residue, which was purified with silica gel column; eluting with CH₂Cl₂/MeOH=15:1 produced the desired compound CYD-2-49 (120 mg, 62%) as a blue foam. ¹H-NMR (600 MHz, CDCl₃/CD₃OD) δ 10.79 (m, 1H), 10.69 (m, 1H), 8.18 (m, 2H), 7.59 (m, 2H), 7.13 (d, 1H, J=9.6 Hz), 7.07 (d, 1H, J=9.6 Hz), 3.93 (m, 1H), 3.68 (m, 5H), 3.62 (m, 1H), 3.46 (m, 1H), 3.35 (m, 3H), 2.46 (m, 6H), 1.85 (m, 2H). ¹³C-NMR (150 MHz, CDCl₃/CD₃OD) δ 178.2, 177.9, 142.3, 142.1, 130.3, 130.2, 128.1, 128.0, 121.9, 121.8, 119.7, 105.8, 105.4, 66.7, 62.9 (3C), 60.2, 52.1, 49.5, 41.1, 36.6, 22.3.

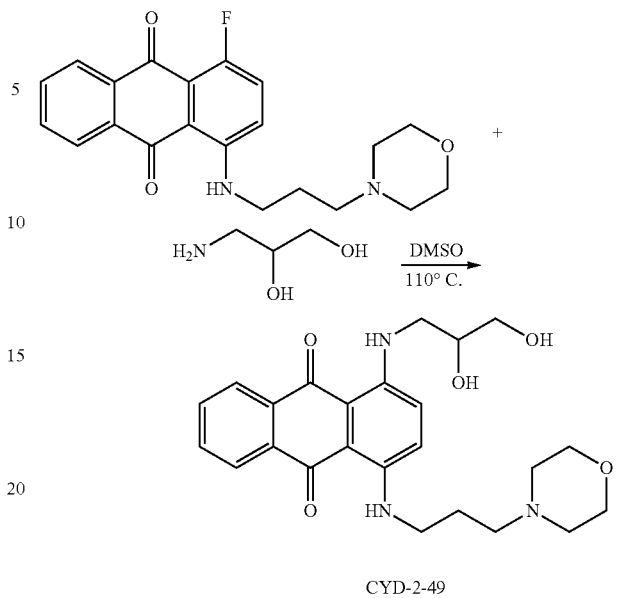

CYD-2-49

1-[2-(1-Methyl-pyrrolidin-2-yl)-ethylamino]-4-(3-morpholin-4-yl-propylamino)-anthraquinone (CYD-2-50)

To a solution of 1-fluoro-4-(3-morpholin-4-yl-propylamino)anthraquinone (170.0 mg, 0.46 mmol) in anhydrous DMSO (6 mL) was added 2-(1-methyl-pyrrolidin-2-yl)ethylamine (119.3 mg, 0.93 mmol). After stirring at 110° C. for 5 hrs, TLC analysis indicated that the starting material disappeared. The reaction mixture was quenched with water (10 mL), and extracted with ethyl acetate (20 mL) for three times. The combined organic phases were washed with brine, and dried with anhydrous Na₂SO₄. The removal of the solvent under vacuum gave a blue residue, which was purified with silica gel column; eluting with CH₂Cl₂/MeOH=12:1 afforded the desired compound CYD-2-50 (106 mg, 48%) as a blue foam. ¹H-NMR (600 MHz, CD₃OD) δ 8.05 (m, 2H), 7.58 (m, 2H), 6.80 (q, 2H, J=10.2 Hz and 20.4 Hz), 3.67 (t, 4H, J=4.2 Hz), 3.14 (m, 4H), 3.04 (m, 1H), 2.41 (m, 6H), 2.31 (s, 3H), 2.21 (m, 2H), 2.02 (m, 2H), 1.75 (m, 4H), 1.53 (m, 2H). ¹³C-NMR (150 MHz, CD₃OD) δ 181.0, 180.9, 145.6, 145.4, 134.1 (2C), 131.3, 125.4 (2C), 123.1, 122.9, 108.8, 108.7, 66.3, 64.3, 56.4, 56.0, 53.4 (2C), 40.2, 39.8, 39.3 (2C), 32.8, 30.3, 25.9, 21.2.

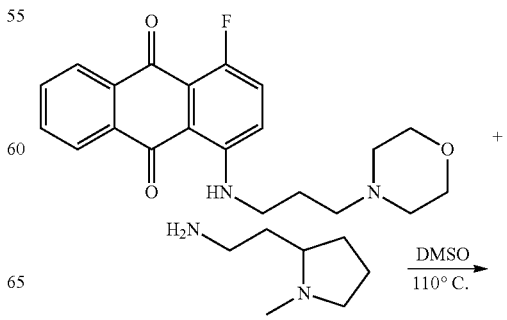

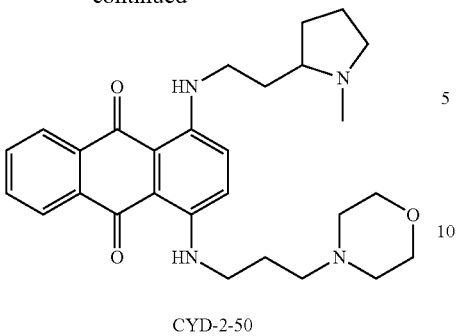

CYD-2-50

(S)-1-(3-Chloro-2-hydroxypropylamino)-4-(3-morpholinopropylamino)anthracene-9,10-dione (CYD-2-77-1) and 1-(3-Hydroxy-azetidin-1-yl)-4-(3-morpholin-4-yl-propylamino)anthraquinone (CYD-2-77-2)

To a solution of (S)-1-amino-3-chloro-2-propanol hydrochloride (195.0 mg, 1.33 mmol) in methanol (8 mL) was added Et$_3$N (135.0 mg, 1.33 mmol). The resulting mixture was stirred at rt for half an hour, and then the solvent was removed to give an oil residue. To a solution of 1-fluoro-4-(3-morpholin-4-yl-propylamino)anthraquinone (464.4 mg, 1.27 mmol) in DMSO (10 mL) was added the basified (S)-1-amino-3-chloro-2-propanol. After stirring at 110° C. for 3.5 hrs, TLC analysis demonstrated that the reaction was complete. The reaction mixture was quenched with water (10 mL) and extracted with ethyl acetate (20 mL) for 3 times. The combined organic phases were washed with brine (15 mL) and dried with anhydrous Na$_2$SO$_4$. The solvent was removed in vacuo, and the resulting residue was purified with silica gel column; elution with CH$_2$Cl$_2$/MeOH=30:1 provided the desired product CYD-2-77-1 (180 mg, 32%) as a blue solid and CYD-2-77-2 (70 mg, 13%) as a blue foam. CYD-2-77-1: $^1$H-NMR (600 MHz, CDCl$_3$) δ 10.74 (t, 1H, J=6.0 Hz), 10.48 (t, 1H, J=4.8 Hz), 8.10 (dd, 2H, J=7.2 Hz and 19.8 Hz), 7.56 (m, 2H), 6.79 (d, 1H, J=9.6 Hz), 6.66 (d, 1H, J=9.6 Hz), 4.16 (br s, 1H), 4.15 (s, 1H), 3.73 (m, 6H), 3.50 (m, 1H), 3.37 (m, 1H), 3.16 (m, 2H), 2.46 (t, 6H, J=7.2 Hz), 1.84 (m, 2H). $^{13}$C-NMR (150 MHz, CDCl$_3$) δ 181.7, 181.1, 145.8, 145.6, 134.1, 133.9, 131.7, 131.5, 125.7 (2C), 122.9, 122.8, 109.7, 109.0, 70.3, 66.8 (2C), 56.1, 53.6 (2C), 46.8, 45.9, 40.6, 26.4. CYD-2-77-2: $^1$H-NMR (600 MHz, CDCl$_3$) δ 10.32 (s, 1H), 8.22 (d, 1H, J=7.8 Hz), 8.12 (d, 1H, J=6.6 Hz), 7.64 (m, 2H), 6.97 (s, 1H), 6.83 (m, 1H), 4.66 (s, 1H), 4.21 (t, 2H, J=7.8 Hz), 3.74 (s, 7H), 3.32 (s, 2H), 2.48 (d, 6H, J=5.4 Hz), 1.88 (t, 2H, J=6.6 Hz). $^{13}$C-NMR (150 MHz, CDCl$_3$) δ 183.2, 181.0, 146.8, 144.5, 134.6, 134.2, 132.1 (2C), 125.9, 125.8, 125.4, 120.1, 115.1, 110.9, 66.8 (2C), 63.2, 61.6, 56.2, 53.6 (3C), 40.8, 26.4.

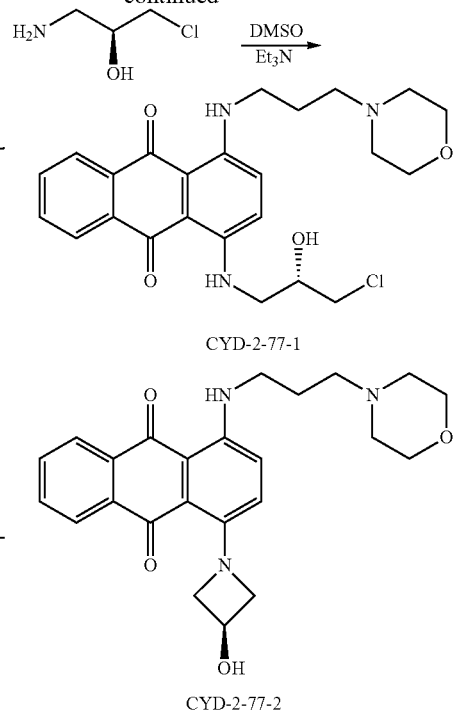

(S)-1-(3-Morpholinopropylamino)-4-(oxiran-2-ylmethylamino)anthracene-9,10-dione (CYD-2-80)

To a solution of CYD-2-77-1 (118.0 mg, 0.25 mmol) in 1,4-dioxane (4 mL) was added a solution of KOH in EtOH (3 mL, 0.5 M). After stirring at rt for 15 min, TLC analysis demonstrated that the starting material disappeared. The reaction mixture was diluted with dichloromethane (20 mL), washed with water (10 mL) and dried with anhydrous Na$_2$SO$_4$. The solvent was removed in vacuo, and the resulting residue was purified with preparative TLC; elution with CH$_2$Cl$_2$/MeOH=35:1 provided the desired product CYD-2-80 (100 mg, 92%) as a blue foam. $^1$H-NMR (600 MHz, CDCl$_3$) δ 10.75 (s, 1H), 10.69 (s, 1H), 8.29 (d, 2H, J=1.8 Hz), 7.67 (d, 2H, J=3.0 Hz), 7.18 (d, 2H, J=13.8 Hz), 3.73 (s, 5H), 3.50 (m, 1H), 3.39 (s, 2H), 3.22 (s, 1H), 2.84 (s, 1H), 2.71 (s, 1H), 2.47 (t, 6H, J=6.6 Hz), 1.88 (t, 2H, J=6.6 Hz). $^{13}$C-NMR (150 MHz, CDCl$_3$) δ 182.7, 182.1, 146.2, 145.7, 134.4, 134.2, 132.0, 131.9, 126.0, 125.9, 123.4, 123.2, 110.2, 109.6, 66.9 (2C), 56.1, 53.7 (2C), 51.2, 44.9, 43.9, 40.7, 26.5.

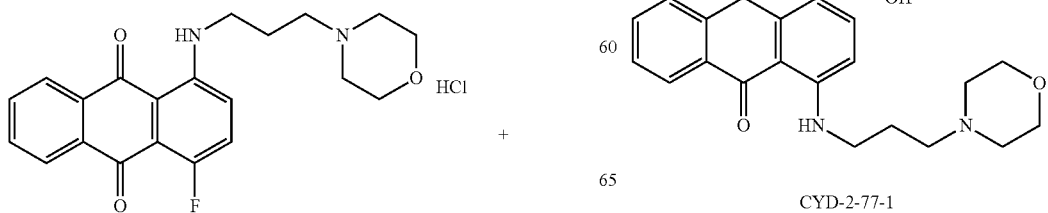

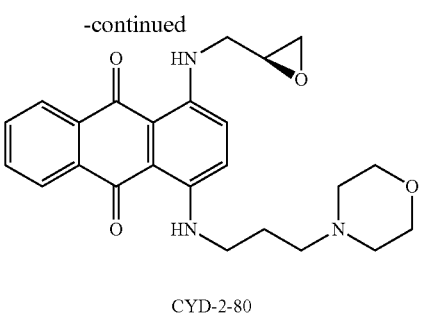

CYD-2-80

1-(2-(2-Hydroxyethylamino)ethylamino)-4-(3-morpholinopropylamino)anthracene-9,10-dione (CYD-3-2)

To a solution of 1-fluoro-4-(3-morpholin-4-yl-propylamino)-anthraquinone (170.0 mg, 0.46 mmol) in anhydrous DMSO (6 mL) was added 2-(2-aminoethylamino)ethanol (96.8 mg, 0.93 mmol). After stirring at 110° C. for 5 hrs, TLC analysis showed that the reaction was complete. The reaction mixture was quenched with water (10 mL), and extracted with ethyl acetate (20 mL) for three times. The combined organic phases were washed with brine, and dried with anhydrous $Na_2SO_4$. The solvent was removed under vacuum to give a blue residue, which was purified with silica gel column; eluting with $CH_2Cl_2$/MeOH=20:1 afforded the desired compound CYD-3-2 (106 mg, 51%) as a blue solid. $^1$H-NMR (600 MHz, $CDCl_3$) δ 10.82 (s, 1H), 10.68 (s, 1H), 8.23 (m, 2H), 7.62 (m, 2H), 6.99 (s, 2H), 3.73 (s, 6H), 3.45 (d, 2H, J=5.4 Hz), 3.35 (d, 2H, J=6.0 Hz), 3.01 (br s, 4H), 2.90 (s, 2H), 2.48 (m, 6H), 1.88 (t, 2H, J=6.6 Hz). $^{13}$C-NMR (150 MHz, $CDCl_3$) δ 182.0, 181.8, 146.0, 145.8, 134.3, 134.2, 131.8, 125.9, 125.8, 123.3, 123.1, 109.8, 109.5, 66.9 (2C), 61.0, 56.1, 53.7 (2C), 51.2, 48.3, 42.4, 40.7, 26.6.

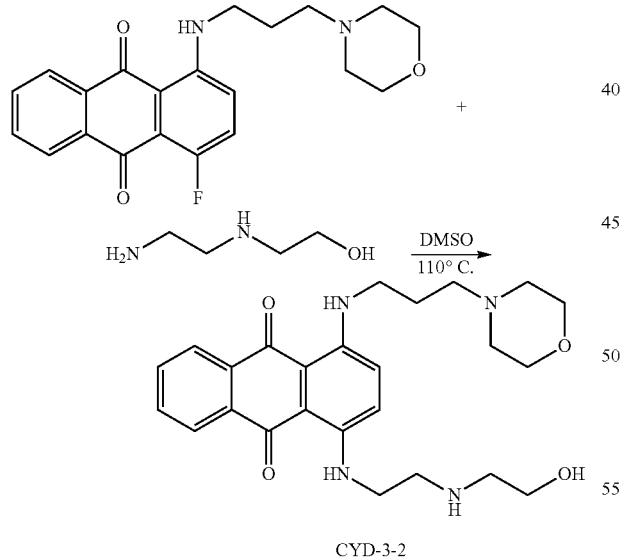

CYD-3-2

1,4-Bis(2-hydroxy-3-morpholinopropylamino)anthracene-9,10-dione (CYD-2-46-1) and 1-(3-chloro-2-hydroxypropylamino)-4-(2-hydroxy-3-morpholinopropylamino)anthracene-9,10-dione (CYD-2-46)

To a solution of 1, 4-diaminoanthraquione (500 mg, 2.09 mmol) in glacial acetic acid (10 mL) at 70° C. was added epichlorohydrin (194.0 mg, 20.98 mmol) all at once. The reaction mixture was stirred at 75° C. for 2 hrs, and the volatiles were removed in vacuo. The resulting mixture was further purified by open column chromatography ($CH_2Cl_2$ with a methanol gradient of up to 2%) to provide a blue solid of the desired compound 1, 4-bis-(3-chloro-2-hydroxy-propylamino)anthraquinone (480 mg, 54%).

To a solution of 1, 4-bis-(3-chloro-2-hydroxy-propylamino)anthraquinone (174.0 mg, 0.41) in ethanol (15 mL) was added morpholine (143.2 mg, 1.64 mmol). After stirring at 80° C. for 72 hrs, TLC showed that most of starting material disappeared. The solvent was removed in vacuo, and the resulting residue was purified with silica gel column; elution with $CH_2Cl_2$/MeOH=30:1 provided the desired product CYD-2-46 (80 mg, 41%) as a blue solid and CYD-2-46-1 (40 mg, 40%) as a blue foam. CYD-2-46: $^1$H-NMR (600 MHz, $CDCl_3$/$CD_3OD$) δ 8.19 (m, 2H), 7.65 (m, 2H), 7.07 (m, 2H), 4.12 (m, 1H), 4.07 (m, 1H), 3.76 (m, 4H), 3.70 (m, 2H), 3.59 (m, 1H), 3.46 (m, 2H), 3.35 (m, 1H), 2.65 (m, 2H), 2.55 (m, 4H). $^{13}$C-NMR (150 MHz, $CDCl_3$/$CD_3OD$) δ 181.7, 181.5, 146.0, 145.8, 134.0, 133.9, 131.7 (2C), 125.6, 125.5, 123.5, 123.2, 109.4, 109.2, 69.7, 66.5 (3C), 66.2, 62.1, 53.6, 46.3, 46.2, 45.1.

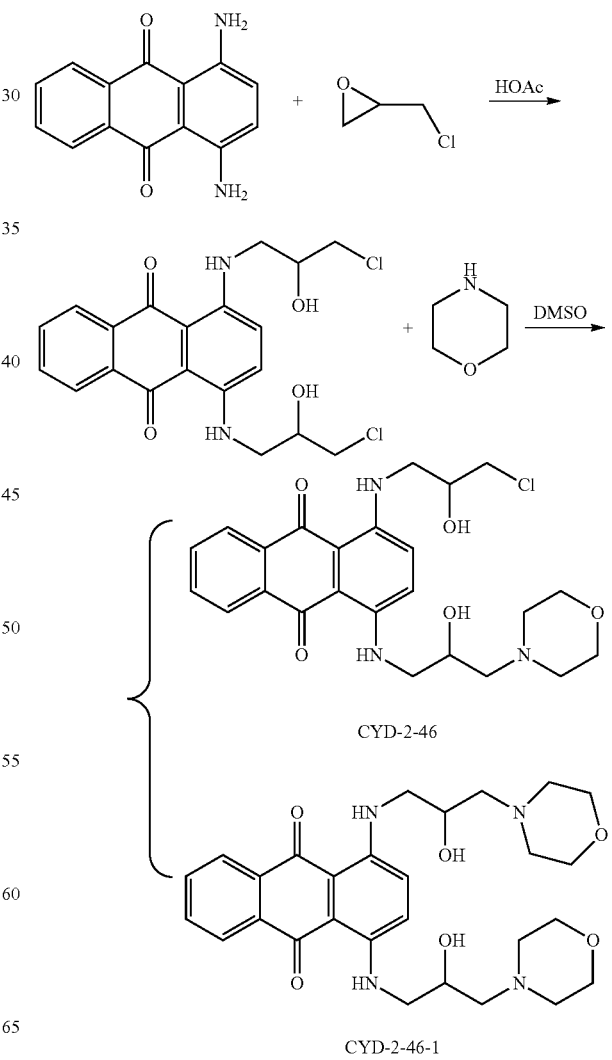

CYD-2-46

CYD-2-46-1

1-(2-Hydroxy-3-morpholinopropylamino)-4-(oxiran-2-ylmethylamino)anthracene-9,10-dione (CYD-2-82)

To a solution of CYD-2-46 (52.0 mg, 0.11 mmol) in a mixture of 1, 4-dioxane (1 mL) and methanol (3 mL) was added a solution of KOH in EtOH (2 mL, 0.5 M). After stirring at rt for 15 min, TLC analysis showed that the starting material disappeared. The reaction mixture was diluted with dichloromethane (20 mL), washed with water (10 mL) and dried with anhydrous Na$_2$SO$_4$. The solvent was removed in vacuo, and the resulting residue was purified with silica gel column; elution with CH$_2$Cl$_2$/MeOH=20:1 provided the desired product CYD-2-82 (48 mg, 100%) as a blue foam. $^1$H-NMR (600 MHz, CDCl$_3$) δ 10.84 (s, 1H), 10.74 (s, 1H), 8.30 (d, 1H, J=1.8 Hz), 7.67 (d, 1H, J=3.0 Hz), 7.20 (m, 1H), 4.05 (d, 1H, J=4.2 Hz), 3.72 (s, 5H), 3.50 (d, 2H, J=4.2 Hz), 3.41 (m, 1H), 3.24 (s, 1H), 2.85 (s, 1H), 2.72 (s, 1H), 2.67 (s, 2H), 2.51 (m, 4H). $^{13}$C-NMR (150 MHz, CDCl$_3$) δ 182.8, 182.5, 146.3, 145.9, 134.3, 134.2, 132.1, 132.0, 126.0 (2C), 123.4 (2C), 110.3, 109.9, 66.9 (3C), 65.6, 62.0, 53.6, 51.2, 46.3, 44.9, 43.9.

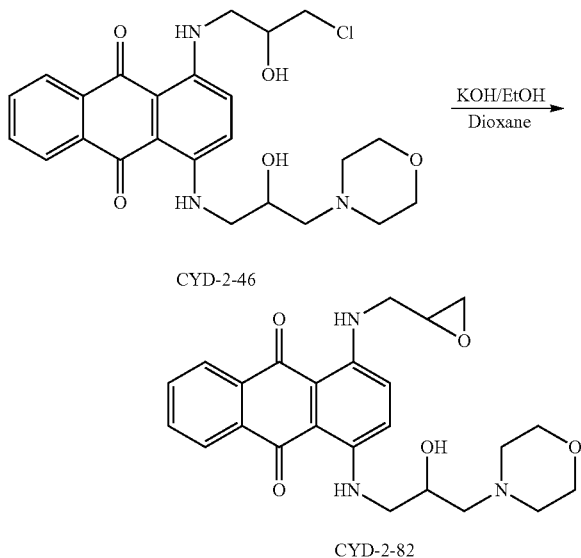

CYD-2-46

CYD-2-82

(S)-tert-Butyl oxiran-2-ylmethylcarbamate

Di-tert-butyl dicarbonate (1.94 g, 8.90 mmol) and triethylamine (1.36 g, 13.69 mmol) were dissolved in dichloromethane (20 mL), and the resulting solution was cooled in an ice bath. The solid of (S)-1-amino-3-chloro-2-propanol hydrochloride (1.0 g, 6.84 mmol) was added in portions. The ice bath was removed and the reaction mixture was stirred at room temperature for 24 hrs. TLC analysis demonstrated the reaction was complete. The white slurry was cooled in an ice bath again, and a solution of KOH in methanol was added. The ice bath was removed again and stirring was kept for an additional hour. The solvent methanol was removed, and the residue was dissolved in ethyl acetate (30 mL), washed with water (15 mL) and dried with anhydrous Na$_2$SO$_4$. The solvent was removed in vacuo, and the resulting residue was purified with silica gel column; elution with CH$_2$Cl$_2$/MeOH=60:1 afforded the desired product (850 mg, 71%) as a colorless oil.

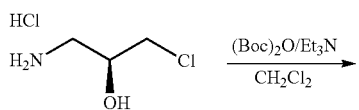

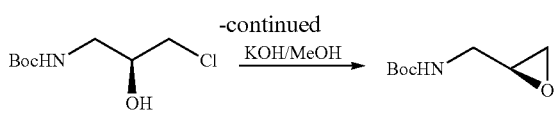

(S)-tert-Butyl 3-(4-acetylpiperazin-1-yl)-2-hydroxypropylcarbamate

A mixture of 1-acetylpiperazine (555 mg, 4.33 mmol) and (S)-tert-butyl oxiran-2-ylmethylcarbamate (250.0 mg, 1.44 mmol) was dissolved in THF (5 mL). After stirring at 55° C. for 24 hrs, TLC analysis displayed that reaction was complete. The solvent was removed in vacuo, and the resulting oil residue was purified with silica gel column; elution with CH$_2$Cl$_2$/MeOH=20:1 afforded the desired product (S)-tert-butyl 3-(4-acetylpiperazin-1-yl)-2-hydroxypropylcarbamate (400 mg, 92%) as a colorless oil.

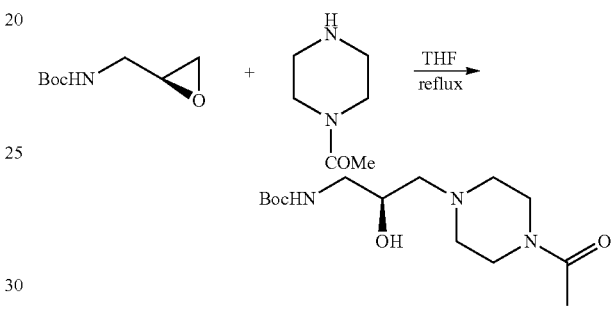

(S)-1-(3-Chloro-2-hydroxypropylamino)-4-fluoroanthracene-9,10-dione. To a solution of 1, 4-difluoroanthraquione (500 mg, 2.04 mmol) in anhydrous DMSO (6 mL) was added (S)-1-amino-3-chloro-2-propanol hydrochloride (448.4 mg, 3.09 mmol) and Et$_3$N (621.4 mg, 6.14 mmol) under nitrogen atmosphere. The resulting mixture was stirred at room temperature for 3 hrs, and then heated at 90° C. for another 5 hrs. The reaction was monitored by TLC analysis in ethyl acetate, indicating that the reaction was complete. The reaction mixture was then quenched with water (10 mL), and extracted with ethyl acetate (20 mL) for three times. The combined organic phases were washed with brine, and dried with anhydrous Na$_2$SO$_4$. The solvent was removed under vacuum to give a red residue, which was purified with silica gel column; eluting with EtOAc/hexane=1:2 afforded the desired compound (S)-1-(3-chloro-2-hydroxypropylamino)-4-fluoroanthracene-9, 10-dione (300 mg, 44%) as a red solid.

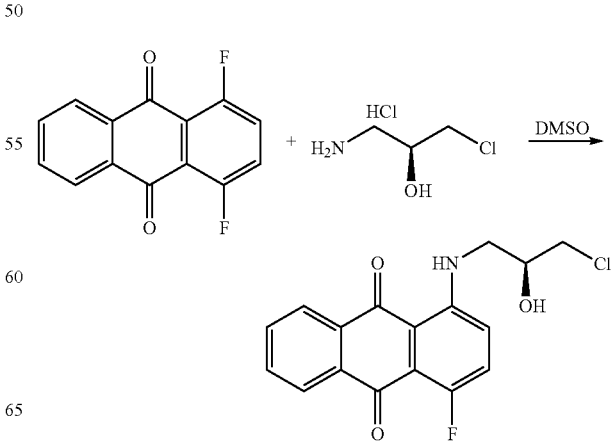

1-((S)-3-(4-Acetylpiperazin-1-yl)-2-hydroxypropylamino)-4-((S)-3-chloro-2-hydroxypropylamino)anthracene-9,10-dione To a solution of (S)-tert-butyl 3-(4-acetylpiperazin-1-yl)-2-hydroxypropylcarbamate (260 mg, 0.86 mmol) in dichloromethane (4 mL) was added TFA (1 mL) at 0° C. The resulting mixture was stirred at rt for 3 hrs. TLC analysis showed that the reaction mixture was complete. The reaction solvent was removed under vacuum to give an oil residue, which was dissolved in methanol (3 mL) and basified with excess of saturated NaHCO$_3$ aqueous solution. The removal of the solvent gave an oil residue, which was dissolved in a mixture of dichloromethane (2 mL) and methanol (2 mL). The solid was removed by filtration, and the filtrate was concentrated to give the desired compound (S)-1-(4-(3-amino-2-hydroxypropyl)piperazin-1 yl)ethanone as an oil residue, which was used directly in the next step without further purification.

To a solution of (S)-1-(3-chloro-2-hydroxypropylamino)-4-fluoroanthracene-9, 10-dione (191.7 mg, 0.57 mmol) in anhydrous DMSO (6 mL) was added the prepared (S)-1-(4-(3-amino-2-hydroxypropyl)piperazin-1-yl)ethanone. After stirring at 110° C. for 5 hrs, TLC analysis showed that the reaction was complete. The reaction mixture was quenched with water (10 mL), and extracted with ethyl acetate (20 mL) for three times. The combined organic phases were washed with brine (20 mL), and dried with anhydrous Na$_2$SO$_4$. The solvent was removed under vacuum to give a blue residue, which was purified with silica gel column; eluting with EtOAc/MeOH/Et$_3$N=3:1:1 afforded the desired compound CYD-2-71-1 (50 mg, 18%) as a blue foam. $^1$H-NMR (600 MHz, CDCl$_3$/CD$_3$OD) δ 8.24 (dd, 2H, J=4.8 Hz and 9.0 Hz), 7.68 (dd, 2H, J=3.6 Hz and 6.0 Hz), 7.16 (s, 2H), 4.11 (m, 2H), 3.66 (m, 5H), 3.52 (m, 4H), 3.40 (m, 1H), 2.59 (m, 6H), 2.10 (s, 3H). $^{13}$C-NMR (150 MHz, CDCl$_3$) δ 182.0, 181.9, 169.6, 146.1, 145.9, 134.1, 134.0, 131.9 (2C), 125.7 (2C), 123.6, 123.4, 109.6, 109.4, 69.8, 66.5, 61.4, 53.3, 52.9, 46.3, 46.0 (2C), 45.3, 41.3, 20.7.

1-((S)-3-(4-Acetylpiperazin-1-yl)-2-hydroxypropylamino)-4-((S)-oxiran-2-ylmethylamino)anthracene-9,10-dione (CYD-2-90)

To a solution of CYD-2-77-1 (40.0 mg, 0.077 mmol) in 1,4-dioxane (6 mL) was added a solution of KOH in EtOH (2 mL, 0.5 M). After stirring at rt for 15 min, TLC analysis showed that the starting material was gone. The reaction mixture was diluted with CH$_2$Cl$_2$ (20 mL), washed with water (10 mL) and dried with anhydrous Na$_2$SO$_4$. The solvent was removed in vacuo, and the resulting residue was purified with silica gel column; elution with CH$_2$Cl$_2$/MeOH=15:1 provided the desired product CYD-2-90 (36 mg, 77%) as a blue foam. $^1$H-NMR (600 MHz, CDCl$_3$) δ 10.83 (s, 1H), 10.73 (s, 1H), 8.29 (s, 2H), 7.67 (s, 2H), 7.21 (s, 2H), 4.05 (s, 1H), 3.73 (m, 1H), 3.63 (d, 2H, J=19.2 Hz), 3.45 (m, 5H), 3.23 (s, 1H), 2.84 (s, 1H), 2.72 (s, 1H), 2.60 (m, 3H), 2.47 (m, 3H), 2.08 (s, 3H). $^{13}$C-NMR (150 MHz, CDCl$_3$) δ 182.9, 182.6, 168.9, 146.3, 145.9, 134.4, 134.3, 132.2, 132.1, 126.1 (2C), 123.4 (2C), 110.4, 110.2, 65.2, 61.5, 53.4, 52.9, 51.2, 46.4, 46.3, 45.0, 44.0, 41.4, 21.2.

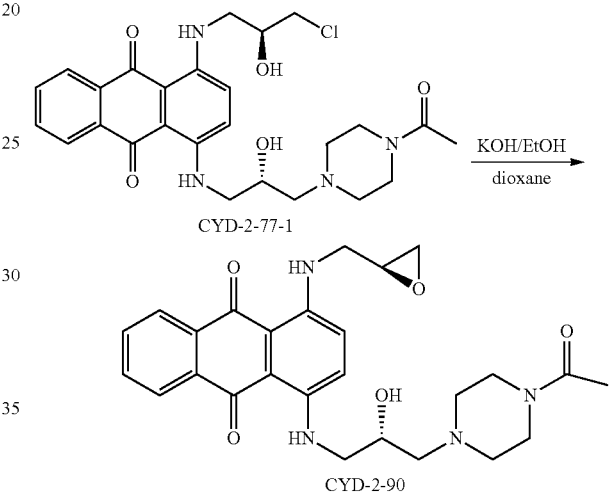

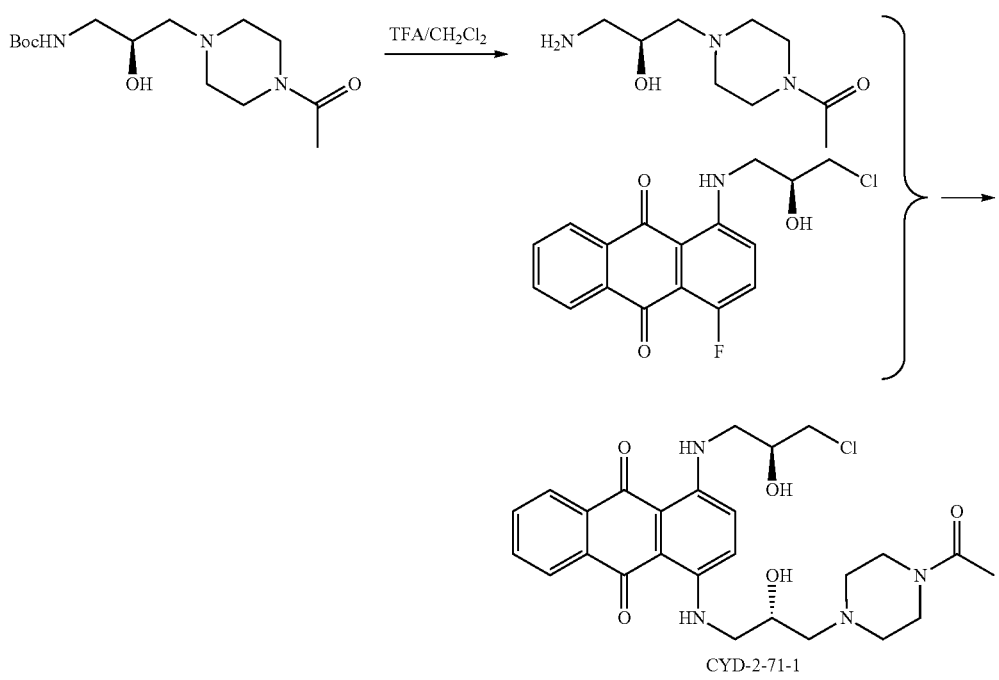

(S)-tert-Butyl 2-hydroxy-3-(piperidin-1-yl)propyl-carbamate

A mixture of piperidine (442.4 mg, 5.19 mmol) and (S)-tert-butyl oxiran-2-ylmethylcarbamate (300.0 mg, 1.73 mmol) dissolved in THF (5 mL) was stirring at 55° C. for 24 hrs. After that, TLC analysis showed that the reaction was complete. The solvent was removed in vacuo, and the resulting oil residue was purified with silica gel column; elution with $CH_2Cl_2/MeOH=20:1$ afforded the desired product (S)-tert-butyl 2-hydroxy-3-(piperidin-1-yl)propylcarbamate (400 mg, 89%) as a colorless oil.

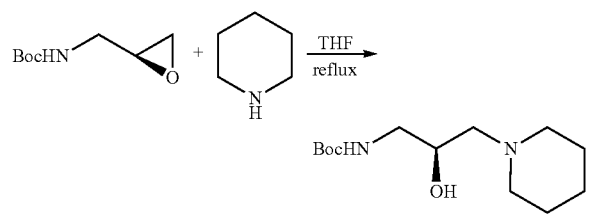

(S)-1-fluoro-4-(2-hydroxy-3-(piperidin-1-yl)propylamino)anthracene-9,10-dione To a solution of (S)-tert-butyl 2-hydroxy-3-(piperidin-1-yl)propylcarbamate (400 mg, 1.55 mmol) in dichloromethane (4 mL) was added TFA (1 mL) at 0° C. The resulting mixture was stirred at rt for 3 hrs. TLC analysis showed that the reaction mixture was complete. The reaction solvent was removed under vacuum to give an oil residue, which was dissolved in methanol (3 mL) and basified with excess of saturated $NaHCO_3$ aqueous solution. The solvent was removed again to give an oil residue, which was dissolved in a mixture of dichloromethane (2 mL) and methanol (2 mL). The solid was removed by filtration, and the filtrate was concentrated to give the desired compound (S)-1-amino-3-(piperidin-1-yl)propan-2-ol as oil residue, which was used in the next step without further purification.

To a solution of 1,4-difluoroanthraquione (378.0 mg, 1.55 mmol) in anhydrous DMSO (6 mL) was added the prepared (S)-1-amino-3-(piperidin-1-yl)propan-2-ol. After stirring at 60° C. for 3 hrs, TLC analysis showed that the reaction was complete. The reaction mixture was quenched with water (10 mL), and extracted with ethyl acetate (20 mL) for three times. The combined organic phases were washed with brine (20 mL), and dried with anhydrous $Na_2SO_4$. The solvent was removed under vacuum to give a red residue, which was purified with silica gel column; eluting with $CH_2Cl_2/MeOH=3:1$ afforded the desired compound (290 mg, 49%) as a red foam.

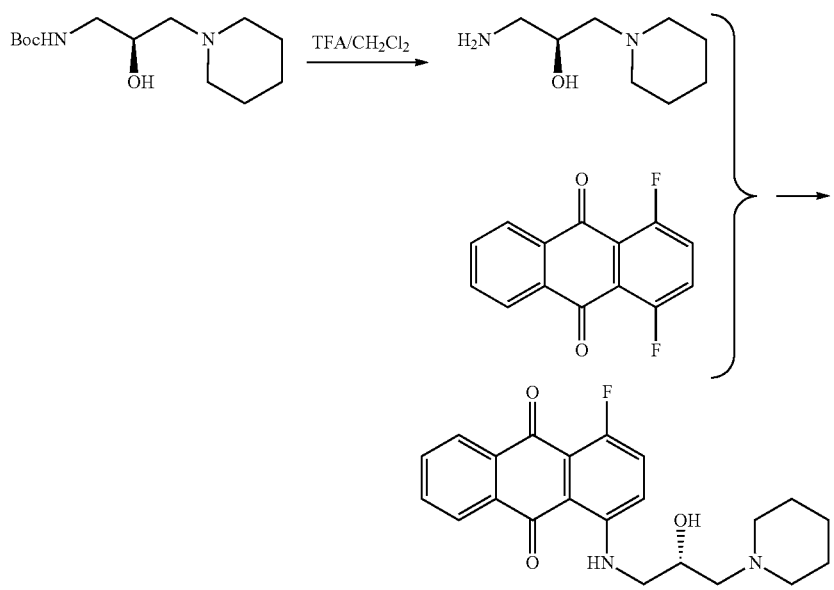

1-((S)-3-Chloro-2-hydroxypropylamino)-4-((S)-2-hydroxy-3-(piperidin-1-yl)propylamino)anthracene-9,10-dione (CYD-2-87-1) and (S)-1-(2-hydroxy-3-(piperidin-1-yl)propylamino)-4-(3-hydroxyazetidin-1-yl)anthracene-9,10-dione (CYD-2-87-2)

To a solution of (S)-1-fluoro-4-(2-hydroxy-3-(piperidin-1-yl)propylamino)anthracene-9,10-dione (290.0 mg, 0.75 mmol) in anhydrous DMSO (8 mL) was added (S)-1-amino-3-chloro-2-propanol hydrochloride (221.4 mg, 1.51 mmol) and $Et_3N$ (153.4 mg, 1.51 mmol). After stirring at 110° C. for 5 hrs, TLC analysis showed that the reaction was complete. The reaction mixture was quenched with water (10 mL), and extracted with ethyl acetate (20 mL) for three times. The combined organic phases were washed with brine, and dried with anhydrous $Na_2SO_4$. The solvent was removed under vacuum to give a blue residue, which was purified with silica gel column; eluting with $CH_2Cl_2/MeOH=10:1$ afforded the desired compound CYD-2-87-1 (80 mg, 23%) as a blue foam and CYD-2-87-2 (90 mg, 27%) as a blue foam. CYD-2-87-1: $^1$H-NMR (600 MHz, DMSO-d6) δ 10.99 (s, 1H), 10.98 (s, 1H), 8.24 (s, 2H), 7.78 (s, 2H), 7.51 (m, 2H), 5.67 (s, 1H), 4.99 (br s, 1H), 3.95 (s, 1H), 3.87 (s, 1H), 3.66 (m, 3H), 3.57 (m, 1H), 3.46 (m, 1H), 3.38 (m, 1H), 2.38 (m, 5H), 1.51 (s, 4H), 1.37 (s, 2H). $^{13}$C-NMR (150 MHz, DMSO-d6) δ 185.9, 185.6, 151.6, 151.2, 139.1, 139.0, 137.6, 137.3, 131.1, 130.6, 130.2, 129.7, 113.8, 113.5, 74.6, 72.0, 67.8, 60.0 (2C), 52.5, 52.0, 50.7, 30.8 (2C), 29.1. CYD-2-87-2: $^1$H-NMR (600 MHz, CDCl$_3$) δ 10.4 (s, 1H), 8.24 (d, 1H, J=6.6 Hz), 8.13 (d, 1H, J=6.0 Hz), 7.63 (m, 2H), 7.05 (d, 1H, J=8.4 Hz), 6.84 (d, 1H, J=9.0 Hz), 4.65 (s, 1H), 4.20 (s, 2H), 4.01 (s, 1H), 3.75 (d, 2H, J=7.8 Hz), 3.34 (m, 4H), 2.61 (s, 2H), 2.42 (m, 4H), 1.58 (s, 4H), 1.45 (s, 2H). $^{13}$C-NMR (150 MHz, CDCl$_3$) δ 183.6, 181.2, 147.0, 144.6, 134.7, 134.3, 132.2 (2C), 126.0 (2C), 125.3, 120.3, 115.4, 111.4, 65.7, 63.3, 63.2, 62.2, 61.9, 54.7, 46.7, 26.0 (2C), 24.2.

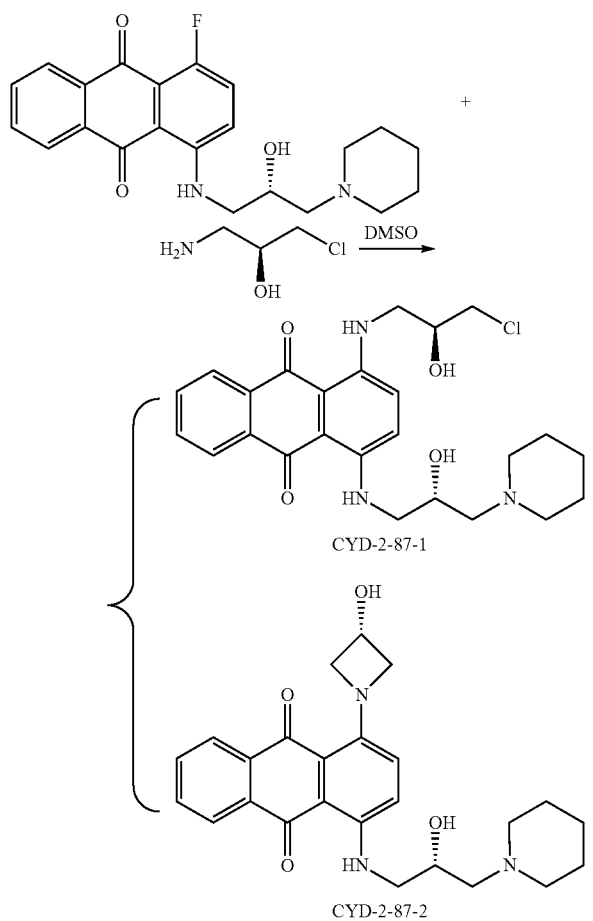

1-((S)-2-Hydroxy-3-(piperidin-1-yl)propylamino)-4-((S)-oxiran-2-ylmethylamino) anthracene-9,10-dione (CYD-2-88)

To a solution of CYD-2-87-1 (65.0 mg, 0.13 mmol) in 1,4-dioxane (4 mL) was added a solution of KOH in EtOH (2 mL, 0.5 M). After stirring at rt for 15 min, TLC analysis showed that the starting material was gone. The reaction mixture was diluted with dichloromethane (20 mL), washed with water (10 mL) and dried with anhydrous Na$_2$SO$_4$. The solvent was removed in vacuo, and the resulting residue was purified with silica gel column; elution with CH$_2$Cl$_2$/MeOH=15:1 provided the desired product CYD-2-88 (50 mg, 83%) as a blue foam. $^1$H-NMR (600 MHz, CDCl$_3$) δ 10.85 (s, 1H), 10.7 (s, 1H), 8.31 (m, 2H), 7.67 (m, 2H), 7.25 (m, 2H), 4.00 (br s, 2H), 3.73 (d, 1H, J=12.6 Hz), 3.48 (m, 3H), 3.23 (s, 1H), 2.84 (s, 1H), 2.71 (s, 1H), 2.60 (s, 2H), 2.44 (s, 2H), 2.35 (s, 2H), 1.44 (s, 4H), 1.25 (s, 2H). $^{13}$C-NMR (150 MHz, CDCl$_3$) δ 183.0, 182.5, 146.5, 145.9, 134.5, 134.3, 132.2, 132.0, 126.1, 126.0, 123.6, 123.4, 110.4, 110.1, 65.8, 62.1, 54.7, 51.2, 46.6, 45.0, 44.0, 26.1 (2C), 24.2.

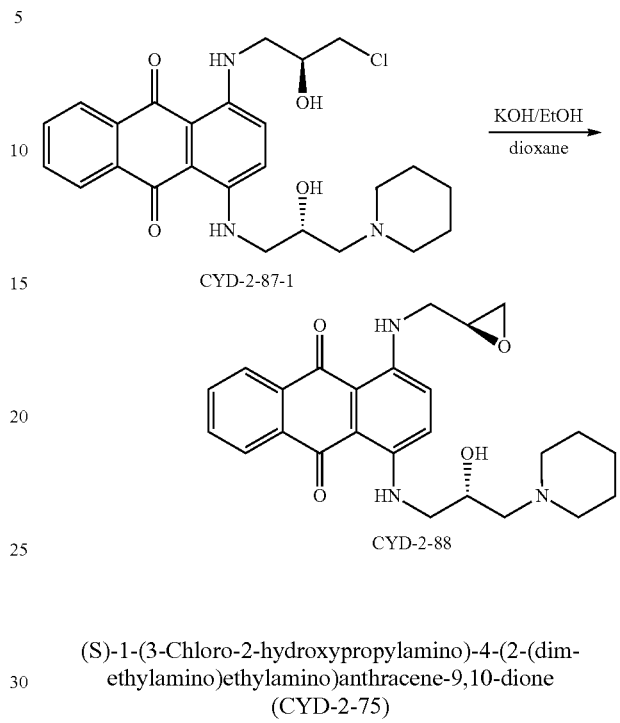

(S)-1-(3-Chloro-2-hydroxypropylamino)-4-(2-(dimethylamino)ethylamino)anthracene-9,10-dione (CYD-2-75)

To a solution of (S)-1-(3-chloro-2-hydroxypropylamino)-4-fluoroanthracene-9, 10-dione (138.0 mg, 0.41 mmol) in anhydrous DMSO (6 mL) was added N,N-dimethylethane-1, 2-diamine (72.8 mg, 0.82 mmol). After stirring at 110° C. for 3.5 hrs, TLC analysis showed that the starting material was gone. The reaction mixture was quenched with water (10 mL), and extracted with ethyl acetate (20 mL) for three times. The combined organic phases were washed with brine (20 mL), and dried with anhydrous Na$_2$SO$_4$. The solvent was removed under vacuum to give a blue residue, which was purified with silica gel column; eluting with CH$_2$Cl$_2$/MeOH=15:1 afforded the desired compound CYD-2-75 (72 mg, 43%) as a blue foam. $^1$H-NMR (600 MHz, CDCl$_3$/CD$_3$OD) δ 10.8 (m, 1H), 10.6 (m, 1H), 8.21 (m, 2H), 7.65 (m, 2H), 7.13 (d, 1H, J=9.6 Hz), 7.03 (d, 1H, J=9.6 Hz), 4.12 (t, 1H, J=5.4 Hz), 3.70 (d, 2H, J=4.8 Hz), 3.61 (dd, 1H, J=4.8 Hz), 3.45 (m, 3H), 2.67 (m, 2H), 2.37 (s, 6H). $^{13}$C-NMR (150 MHz, CDCl$_3$/CD$_3$OD) δ 182.1, 181.9, 145.8, 145.6, 134.1, 134.0, 131.9, 131.8, 125.7 (2C), 123.4, 123.2, 109.8, 109.4, 69.9, 58.2, 46.5, 46.4, 45.5, 45.2, 40.3.

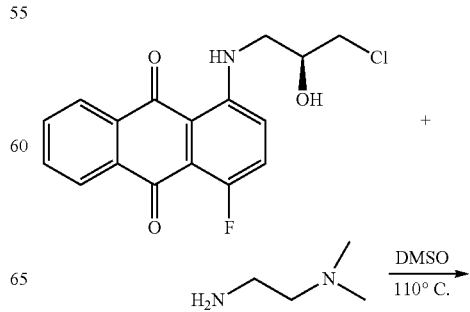

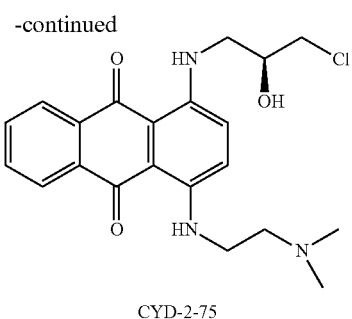

CYD-2-75

(S)-1-(2-(Dimethylamino)ethylamino)-4-(oxiran-2-ylmethylamino)anthracene-9,10-dione (CYD-2-81)

To a solution of CYD-2-75 (50.0 mg, 0.12 mmol) in 1,4-dioxane (4 mL) was added a solution of KOH in EtOH (1.8 mL, 0.5 M). After stirring at rt for 15 min, TLC analysis showed that the starting material disappeared. The reaction mixture was diluted with dichloromethane (20 mL), washed with water (10 mL) and dried with anhydrous $Na_2SO_4$. The solvent was removed in vacuo, and the resulting residue was purified with preparative TLC; elution with $CH_2Cl_2$/MeOH=15:1 provided the desired product CYD-2-81 (20 mg, 44%) as a blue foam. $^1$H-NMR (600 MHz, $CDCl_3$) δ 10.77 (s, 1H), 10.69 (s, 1H), 8.33 (m, 2H), 7.68 (m, 2H), 7.30 (m, 1H), 7.22 (m, 1H), 3.75 (m, 1H), 3.57 (m, 1H), 3.49 (m, 2H), 3.25 (m, 1H), 2.85 (t, 1H, J=4.2 Hz), 2.73 (m, 1H), 2.66 (t, 2H, J=6.6 Hz), 2.34 (s, 6H). $^{13}$C-NMR (150 MHz, $CDCl_3$) δ 183.1, 182.5, 146.0, 145.8, 134.4, 134.2, 132.1, 132.0, 126.1, 126.0, 123.5, 123.3, 110.5, 109.9, 58.5, 51.2, 45.6 (2C), 44.9, 43.9, 41.0.

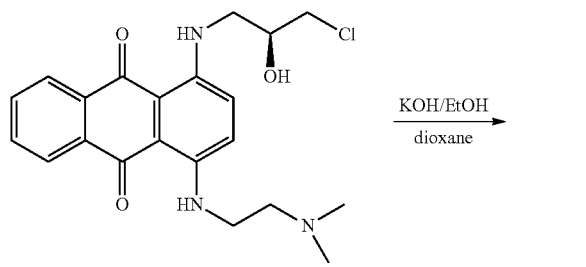

CYD-2-75

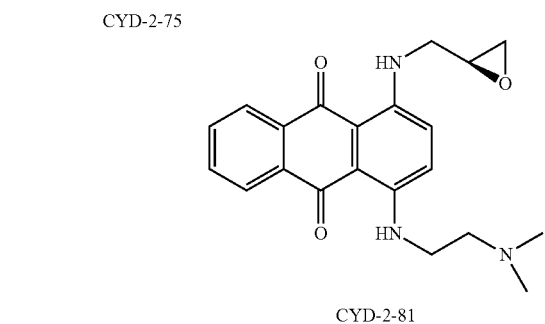

CYD-2-81

(S)-1-(Cyclopropylmethylamino)-4-(2-hydroxy-3-(piperidin-1-yl)propylamino) anthracene-9,10-dione (CYD-2-89)

To a solution of (S)-1-fluoro-4-(2-hydroxy-3-(piperidin-1-yl)propylamino)anthracene-9,10-dione CYD-2-86 (98.0 mg, 0.25 mmol) in anhydrous DMSO (8 mL) was added cyclopropylmethanamine (38.0 mg, 0.53 mmol). After stirring at 110° C. for 3 hrs, TLC analysis showed that the reaction was complete. The reaction mixture was quenched with water (10 mL), and extracted with ethyl acetate (20 mL) for three times. The combined organic phases were washed with brine, and dried with anhydrous $Na_2SO_4$. The solvent was removed under vacuum to give a blue residue, which was purified with silica gel column; eluting with $CH_2Cl_2$/MeOH=20:1 afforded the desired compound CYD-2-89 (100 mg, 90%) as a blue solid. $^1$H-NMR (600 MHz, $CDCl_3$) δ 10.88 (s, 1H), 10.74 (s, 1H), 8.30 (s, 2H), 7.64 (s, 2H), 7.22 (d, 1H, J=9.6 Hz), 7.08 (d, 1H, J=8.4 Hz), 4.04 (d, 1H, J=3.0 Hz), 3.93 (br s, 1H), 3.42 (m, 2H), 3.20 (s, 2H), 2.63 (s, 2H), 2.49 (s, 2H), 2.42 (s, 2H), 1.60 (s, 4H), 1.45 (s, 2H), 1.19 (d, 1H, J=4.8 Hz), 0.64 (d, 2H, J=5.4 Hz), 0.33 (s, 2H). $^{13}$C-NMR (150 MHz, $CDCl_3$) δ 182.3, 182.1, 146.1, 146.0, 134.5, 134.4, 131.9, 131.8, 126.0, 125.9, 123.6, 123.3, 110.0, 109.6, 65.8, 62.2, 54.7, 47.6, 46.7, 25.8 (2C), 24.0, 10.8, 3.77 (2C).

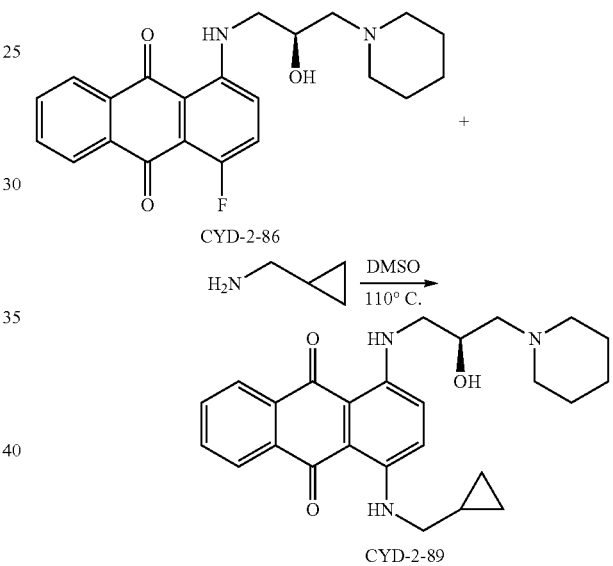

(S)-1-(3-(4-Acetylpiperazin-1-yl)-2-hydroxypropylamino)-4-(3-morpholinopropylamino) anthracene-9,10-dione (CYD-2-85)

A mixture of CYD-2-80 (50 mg, 0.12 mmol) and 1-acetylpiperizine (45.6 mg, 0.35 mmol) dissolved in THF (5 mL) was stirring at 55° C. for 24 hrs. After that, TLC analysis showed that the reaction was complete. The solvent was removed in vacuo, and the resulting oil residue was purified with preparative TLC; elution with $CH_2Cl_2$/MeOH=20:1 afforded the desired product CYD-2-85 (25 mg, 38%) as a blue solid. $^1$H-NMR (600 MHz, $CDCl_3$) δ 10.84 (s, 1H), 10.68 (s, 1H), 8.25 (s, 2H), 7.61 (s, 2H), 7.18 (d, 1H, J=10.2 Hz), 7.13 (d, 1H, J=9.6 Hz), 3.99 (s, 1H), 3.61 (m, 6H), 3.42 (m, 6H), 2.54 (m, 3H), 2.44 (m, 8H), 2.02 (s, 3H), 1.85 (s, 2H). $^{13}$C-NMR (150 MHz, $CDCl_3$) δ 182.5, 182.2, 168.9, 146.2, 146.0, 134.4, 134.3, 132.0, 131.9, 126.0, 125.9, 123.5, 123.3, 110.2, 109.7, 66.9 (2C), 66.2, 61.5, 56.1, 53.7 (2C), 53.4, 52.9, 46.4, 46.2, 41.4, 40.8, 26.6, 21.2.

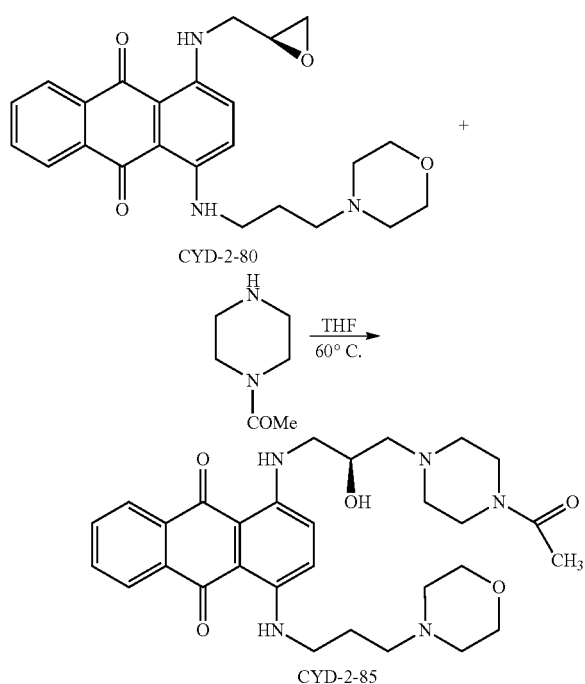

(S)-1-(3-Chloro-2-hydroxypropylamino)-4-(cyclopropylmethylamino)anthracene-9,10-dione (CYD-2-91)

To a solution of (S)-1-(3-chloro-2-hydroxypropylamino)-4-fluoroanthracene-9, 10-dione (120.0 mg, 0.36 mmol) in anhydrous DMSO (6 mL) was added cyclopropylmethanamine (64.0 mg, 0.89 mmol). After stirring at 110° C. for 3 hrs, TLC analysis showed that the starting material was gone. The reaction mixture was quenched with water (10 mL), and extracted with ethyl acetate (20 mL) for three times. The combined organic phases were washed with brine (20 mL), and dried with anhydrous Na$_2$SO$_4$. The solvent was removed under vacuum to give a blue residue, which was purified with silica gel column; eluting with CH$_2$Cl$_2$/MeOH=40:1 afforded the desired compound CYD-2-91 (110 mg, 79%) as a blue foam.

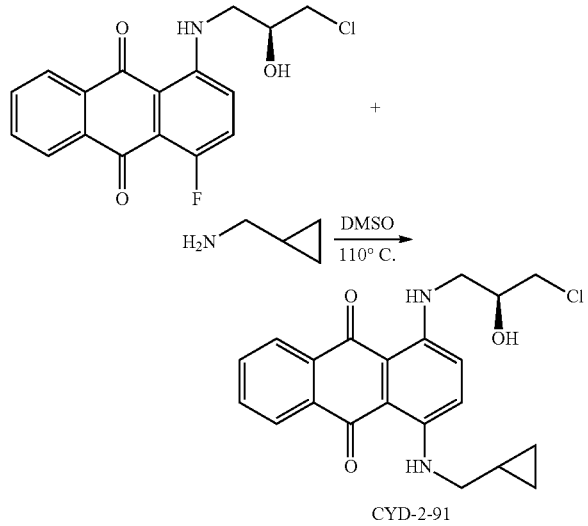

(S)-1-(Cyclopropylmethylamino)-4-(oxiran-2-ylmethylamino)anthracene-9,10-dione (CYD-2-93)

To a solution of CYD-2-91 (110.0 mg, 0.28 mmol) in 1, 4-dioxane (6 mL) was added a solution of KOH in EtOH (4.28 mL, 0.5 M). After stirring at rt for 15 min, TLC analysis showed that the starting material was gone. The reaction mixture was diluted with dichloromethane (20 mL), washed with water (10 mL) and dried with anhydrous Na$_2$SO$_4$. The solvent was removed under vacuum, and the resulting residue was purified with silica gel column; elution with CH$_2$Cl$_2$/MeOH=120:1 provided the desired product CYD-2-93 (85 mg, 85%) as a blue solid. $^1$H-NMR (600 MHz, CDCl$_3$) δ 10.79 (s, 1H), 10.74 (s, 1H), 8.33 (s, 2H), 7.69 (d, 2H, J=1.8 Hz), 7.28 (m, 1H), 7.20 (d, 1H, J=9.0 Hz), 3.73 (m, 1H), 3.58 (m, 1H), 3.26 (m, 3H), 2.84 (s, 1H), 2.72 (s, 1H), 1.23 (m, 1H), 0.66 (m, 2H), 0.34 (s, 2H). $^{13}$C-NMR (150 MHz, CDCl$_3$) δ 183.1, 182.5, 146.2, 145.8, 134.6, 134.3, 132.2, 132.0, 126.1, 126.0, 123.6, 123.4, 110.5, 109.7, 51.3, 47.7, 45.0, 44.0, 10.8, 3.79 (2C).

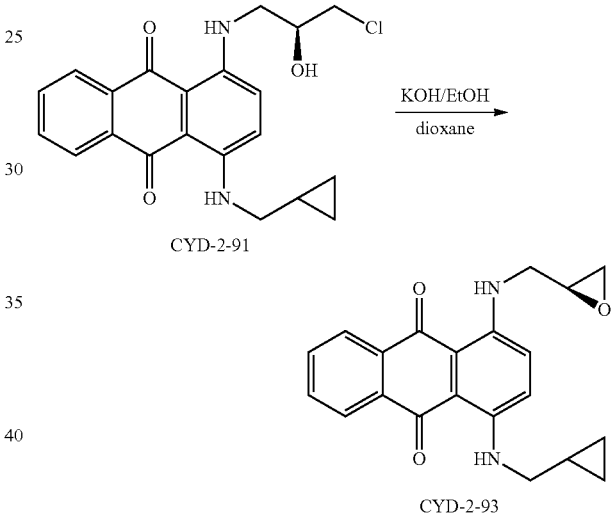

(S)-1-(Cyclopropylmethylamino)-4-(3-(diethylamino)-2-hydroxypropylamino) anthracene-9, 10-dione (CYD-2-94)

A mixture of CYD-2-93 (64.0 mg, 0.18 mmol) and diethylamine (67.0 mg, 0.91 mmol) dissolved in THF (5 mL) was stirring at 55° C. for 24 hrs. After that, TLC analysis showed that the reaction was complete. The solvent was removed in vacuo, and the resulting oil residue was purified with preparative TLC; elution with CH$_2$Cl$_2$/MeOH=30:1 afforded the desired product CYD-2-94 (46 mg, 59%) as a blue solid. $^1$H-NMR (600 MHz, CDCl$_3$) δ 10.95 (s, 1H), 10.80 (s, 1H), 8.35 (m, 2H), 7.68 (m, 2H), 7.32 (d, 1H, J=9.6 Hz), 7.20 (d, 1H, J=9.6 Hz), 3.95 (m, 1H), 3.48 (m, 2H), 3.27 (m, 2H), 2.68 (m, 2H), 2.58 (m, 4H), 1.21 (s, 1H), 1.05 (t, 6H, J=7.2 Hz), 0.65 (m, 2H), 0.34 (m, 2H). $^{13}$C-NMR (150 MHz, CDCl$_3$) δ 182.6, 182.4, 146.2, 146.1, 134.5 (2C), 132.0, 131.9, 126.1, 125, 9, 123.7, 123.4, 110.1, 109.7, 66.2, 57.0, 47.7, 47.1 (2C), 46.7, 11.9 (2C), 10.8, 3.79 (2C).

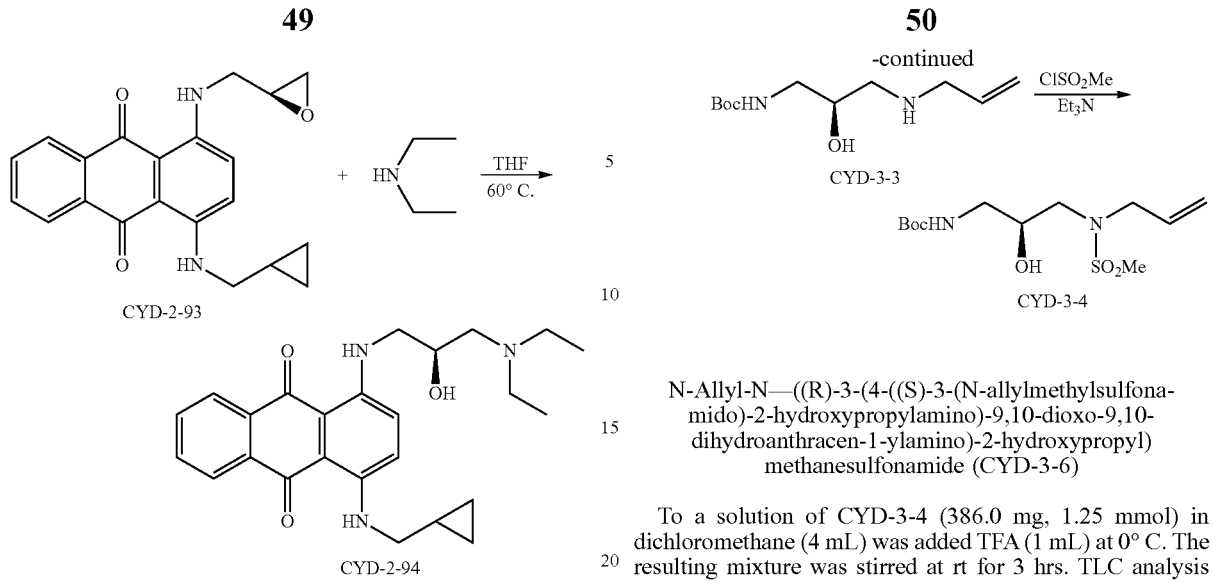

(S)-tert-Butyl 3-(N-allylmethylsulfonamido)-2-hydroxypropylcarbamate (CYD-3-4)

A mixture of allylamine (346.1 mg, 6.06 mmol) and (S)-tert-butyl oxiran-2-ylmethyl carbamate (350.0 mg, 2.02 mmol) dissolved in i-PrOH (6 mL) was stirring at 60° C. for 4 hrs. After that, TLC analysis showed that the reaction was complete. The solvent was removed under vacuum, and the resulting oil residue was purified with silica gel column; elution with CH$_2$Cl$_2$/MeOH=10:1 afforded the desired product CYD-3-3 (320 mg, 68%) as a colorless oil.

To a solution of CYD-3-3 (288 mg, 1.25 mmol) in dichloromethane (6 mL) was added methanesulfonyl chloride (172.1 mg, 1.50 mmol) and Et$_3$N (191.0 mg, 1.87 mmol) at ice-water bath. The resulting mixture was stirred at rt for 2 hrs. After that, TLC analysis showed that the reaction was complete. The reaction mixture was washed with saturated NaHCO$_3$ aqueous solution, followed by brine and dried with anhydrous Na$_2$SO$_4$. The solvent was removed under vacuum, and the resulting residue was purified with silica gel column; elution with CH$_2$Cl$_2$/MeOH=20:1 provided the desired product CYD-3-4 (385.0 mg, 100%) as colorless oil.

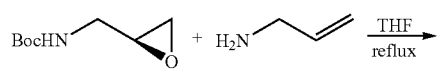

N-Allyl-N—((R)-3-(4-((S)-3-(N-allylmethylsulfonamido)-2-hydroxypropylamino)-9,10-dioxo-9,10-dihydroanthracen-1-ylamino)-2-hydroxypropyl) methanesulfonamide (CYD-3-6)

To a solution of CYD-3-4 (386.0 mg, 1.25 mmol) in dichloromethane (4 mL) was added TFA (1 mL) at 0° C. The resulting mixture was stirred at rt for 3 hrs. TLC analysis showed that the reaction mixture was complete. The reaction solvent was removed under vacuum to give an oil residue, which was dissolved in methanol (3 mL) and basified with excess of saturated NaHCO$_3$ aqueous solution. The removal of the solvent gave an oil residue, which was dissolved in a mixture of dichloromethane (2 mL) and methanol (2 mL). The solid was removed by filtration, and the filtrate was concentrated to give the desired compound CYD-3-5 as oil residue, which was used directly in the next step without further purification.

To a solution of 1, 4-difluoroanthraquione (157.7 mg, 0.64 mmol) in anhydrous DMSO (6 mL) was added CYD-3-5 (260 mg, 1.25 mmol) and Et$_3$N (127.3 mg, 1.25 mmol) under nitrogen atmosphere. The resulting mixture was stirred at 110° C. for 10 hrs. After that, TLC analysis showed that starting material was complete, and the reaction mixture was quenched with water (10 mL), and extracted with ethyl acetate (20 mL) for three times. The combined organic phases were washed with brine, and dried with anhydrous Na$_2$SO$_4$. The solvent was removed under vacuum to give a blued residue, which was purified with silica gel column; eluting with ethyl acetate afforded the desired compound CYD-3-6 (200 mg, 50%) as a blue solid. $^1$H-NMR (600 MHz, CDCl$_3$) δ 10.59 (s, 2H), 7.93 (d, 2H, J=2.4 Hz), 7.55 (d, 2H, J=2.4 Hz), 6.35 (s, 2H), 5.94 (m, 2H), 5.39 (d, 2H, J=17.4 Hz), 5.33 (d, 2H, J=9.6 Hz), 4.49 (br s, 2H), 4.09 (m, 6H), 3.40 (m, 4H), 3.26 (d, 2H, J=10.8 Hz), 3.12 (d, 2H, J=6.0 Hz), 3.02 (s, 6H). $^{13}$C-NMR (150 MHz, CDCl$_3$) δ 176.0 (2C), 141.2 (2C), 129.0 (2C), 127.6 (2C), 127.0 (2C), 120.9 (2C), 118.0 (2C), 115.2 (2C), 104.1 (2C), 64.2 (2C), 46.7 (2C), 45.9 (2C), 41.6 (2C), 34.3 (2C).

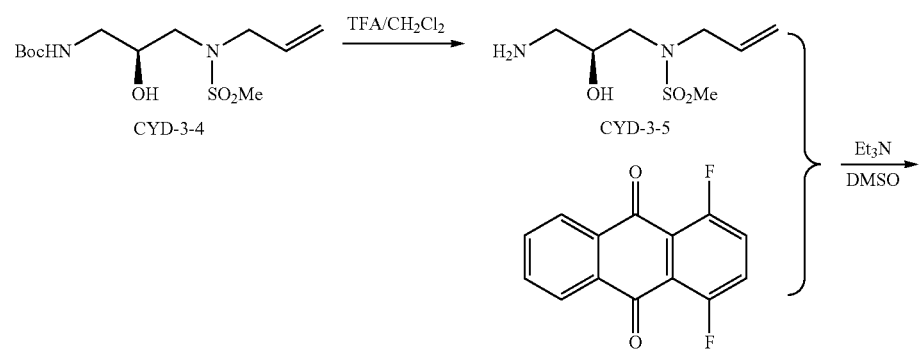

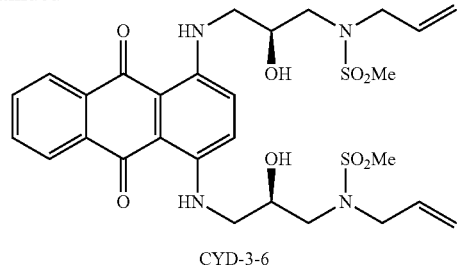

CYD-3-6

Screening of Small Molecules Targeting the BH4 Domain of Bcl2

A library containing approximately 300,000 small molecules from the National Cancer Institute (NCI) was used to dock the structural pocket of the BH4 domain. The small molecules were ranked according to their energy scores. The top 200 small molecules were selected for screening of cytotoxicity in human lung cancer cells by sulforhodamine B (SRB) assay. Among these small molecules, one compound had the most potent activity against human lung cancer cells. This lead compound is small molecule Bcl2 BH4 domain antagonist (BDA-2 or BDA-A2).

The effect of BDA-2 on cell growth and apoptosis was measured by SRB assay and Annexin V/PI binding, respectively, in both small cell lung cancer (SCLC) and non-small cell lung cancer (NSCLC) cell lines that express various levels of endogenous Bcl2. Results indicate that NSCLC cell lines (i.e. H157, Calu-1, H358, H460 and H1975) and SCLC cell lines (i.e. DMS53, DMS153, H146 and H69) that express relatively higher levels of Bcl2 were more sensitive to BDA-2. In contrast, lung cancer cell lines expressing relatively lower or undetectable levels of endogenous Bcl2 (i.e. NSCLC cell lines: A549 and H1299; SCLC cell lines: DMS114 and H128) were less sensitive to BDA-2. It seems that expression levels of Mc1-1 or Bcl-XL did not significantly affect sensitivity of cells to BDA-2. The apoptotic response of BDA-2 may be dependent on the expression levels of Bcl2 in lung cancer cell lines. Importantly, BDA-2 showed less sensitive to normal small airway epithelial cell line (SAEC), indicating a relative selectivity against cancer cells compared to normal cells.

BDA-2 Selectively Binds to Bcl2 at the BH4 Domain and Induces Cell Killing

Purified recombinant WT and a panel of Bcl2 BH domain deletion mutant proteins (i.e. ΔBH1, ΔBH2, ΔBH3 and ΔBH4) were commercially obtained from ProteinX Lab. To directly measure BDA-2/Bcl2 binding, a fluorescence polarization assay with a fluorescent Bak peptide (5'-FAMGQVGRQLAIIGDDINR) was performed. BDA-2 directly binds to Bcl2 with high binding affinity (Ki=3.3±0.73 nM). Deletion of BH1, BH2 or BH3 from Bcl2 protein did not significantly affect its BDA-2 binding. However, the BH4 domain deficient Bcl2 mutant protein (ΔBH4) failed to bind BDA-2. These findings indicate that BDA-2 selectively binds to Bcl2 via the BH4 domain. Importantly, BDA-2 did not bind to other Bcl2 family members, including Bcl-XL, Mc1-1, or Bfl-1/A1, indicating the specificity of its Bcl2 binding.

Structural modeling analysis by computational program reveals that BDA-2 is associated with 8 amino acids (i.e. ASP10, ASN11, ARG12, GLU13, MET16, LYS17, HIS20 and ASP31) in the BH4 domain. A panel of Bcl2 mutants were generated within the BH4 domain at the specific residues that were identified by the initial docking simulations, including D10A, N11A, R12A, E13A, M16A, K17A, H20A and D31A Bcl2 mutants. A compound Bcl2 mutant D10A/N11A/R12A/E13A (AAAA) was created. Recombinant proteins of these mutants were generated for BDA-2/Bcl2 binding analysis using a competitive fluorescence polarization. Studies indicated that single mutation at each individual residue did not significantly reduce Bcl2's ability to bind BDA-2 but AAAA Bcl2 mutant protein had remarkably decreased BDA-2 binding. Second, WT and all Bcl2 mutants were exogenously overexpressed in H1299 cells that express undetectable levels of endogenous Bcl2. Results indicate that overexpression of exogenous WT or each of the Bcl2 mutants in H1299 cells potently inhibited cisplatin-induced apoptotic cell death, indicating that these Bcl2 mutants retain standard anti-apoptotic function. However, overexpression of exogenous WT and each of the Bcl2 single site mutants in H1299 cells failed to prolong cell survival when cells were exposed to BDA-2 and exhibited enhanced sensitivity to BDA-2, indicating that BDA-2 not only overcomes Bcl2's antiapoptotic function but also may convert these Bcl2 proteins into death molecules. In contrast, overexpression of the compound Bcl2 AAAA mutant significantly prolonged cell survival when cells were exposed to BDA-2, suggesting that compound mutations (AAAA) at BDA-2 binding residues lead to a phenotype that is resistant to BDA-2. This suggests that BDA-2 binding to these four amino acids (D10, N11, R12 and E13) in the BH4 domain is important for BDA-2 regulation of Bcl2 and induction of apoptosis.

To determine whether Bcl-2 is the relevant target at the cellular level and whether cell killing is truly dependent on this particular mechanism, Bcl2 was specifically knocked down using three different Bcl2 shRNAs that target different regions in Bcl2 gene in five lung cancer cell lines, including two NSCLC cell lines (H460 and H157) and three SCLC cell lines (DMS53, DMS153 and H146). Stable expression of Bcl2 shRNA1, shRNA2 or shRNA3 efficiently depleted the endogenous Bcl2 in both NSCLC and SCLC cell lines. This effect of shRNA on Bcl2 expression was highly specific because the control shRNA had no effect. Cells expressing Bcl2 shRNA1, shRNA2, shRNA3 or control shRNA were treated with BDA-2 (1 µM) for 72 h.

The level of apoptotic cell death was determined by analysis of Annexin-V/PI binding by FACS. Importantly, depletion of endogenous Bcl2 from these lung cancer cell lines by Bcl2 shRNA1, shRNA2 or shRNA3 resulted in significantly reduced sensitivity of cells to BDA-2.

Whether expression of exogenous Bcl2 can restore the sensitivity of Bcl2-silenced lung cancer cells to BDA-2 and whether the BDA-2/BH4 binding is important for such effect was examined. WT and BDA-2 binding deficient D10A/N11A/R12A/E13A (AAAA) Bcl2 mutant cDNA in pCIneo or vector-only control were transfected into H460 or DMS53 cells expressing Bcl2 shRNA. It has been reported that if the shRNA is directed to the 3' UTR or 5' UTR of the gene, the effect of the shRNA1 can be rescued by ectopically expressing the protein using the wild-type or mutant cDNA. Because Bcl2 shRNA1 targets the 5'UTR of endogenous Bcl2, the silencing effect of shRNA1 on Bcl2 expression could be rescued by transfection of exogenous WT or AAAA Bcl2 mutant. After transfection, cells were treated with BDA-2 or the BH3 mimetic ABT-199 at the indicated concentrations for 72 h. Results reveal that expression of exogenous WT Bcl2 restored sensitivity of cells to both BDA-2 and ABT-199, indicating that both BDA-2 and ABT-199 are selective Bcl2 inhibitors. However, expression of AAAA only restored the sensitivity of cells to ABT-199 but not to BDA-2, indicating that compound mutations in the BH4 domain result in a selective resistance to BDA-2 while maintaining sensitivity to the BH3 mimetic (ABT-199). These data suggest that BDA-2, but not ABT-199, acts as a unique BH4 domain inhibitor. The apoptotic effect of BDA-2 on lung cancer cells requires its BH4 binding.

To test whether BDA-2 reacts with DNA as a crosslinker, electrophoretic mobility shift assay (EMSA) was performed. Cisplatin, a known DNA binding agent, was used as positive control. Plasmid pUC19 DNA was incubated with BDA-2 or cisplatin. Intriguingly, cisplatin but not BDA-2 can bind to pUC19 DNA to cause mobility shift. This helps to rule out the possibility of BDA-2 as DNA binding agent.

BDA-2 Induces Bcl2 Conformational Change and Abrogates Bcl2 Survival Function

A report indicates that the interaction between the nuclear orphan receptor Nur77/TR3 and Bcl2 or the binding of p53 to Bcl2 causes a conformational change in Bcl2 that induces the "exposure" of its own BH3 domain, leading to loss of Bcl2's antiapoptotic activity. Furthermore, removal of the BH4 domain from Bcl2 by caspase 3 results in a conversion of Bcl-2 from a survival protein to a Bax-like death molecule. Since BDA-2 is a BH4 domain binding molecule, its binding to BH4 may result in a similar conformational change in Bcl2 to alter its function.

To test whether BDA-2 directly induces Bcl2 conformational change, an in vitro cell-free assay was employed. Purified recombinant Bcl2 protein was incubated with increasing concentrations of BDA-2 in lysis buffer, followed by immunoprecipitation (IP) using the anti-Bcl2/BH3 domain antibody. Results indicate that addition of BDA-366 enhanced the ability of the Bcl2/BH3 domain-specific antibody to bind Bcl2, and this occurred in a dose-dependent manner. These findings appear to provide direct evidence for the notion that binding of BDA-366 with the BH4 domain is able to alter Bcl2's conformation leading to greater exposure of its own BH3 domain. Since only BDA-366 but not a chemotherapeutic agent (i.e. VP-16 or cisplatin) can directly induce Bcl2 conformational change in a cell-free system, this shows specificity for BDA-366 induction of such conformational change.

Figure 2:
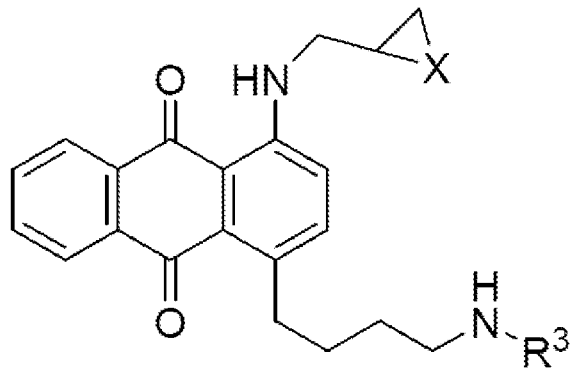
FIG. 2 illustrates the chemical structures of certain embodiments.
Figure 2:
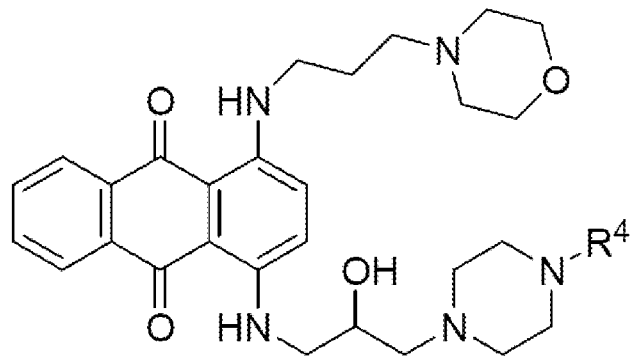
Figure 3:
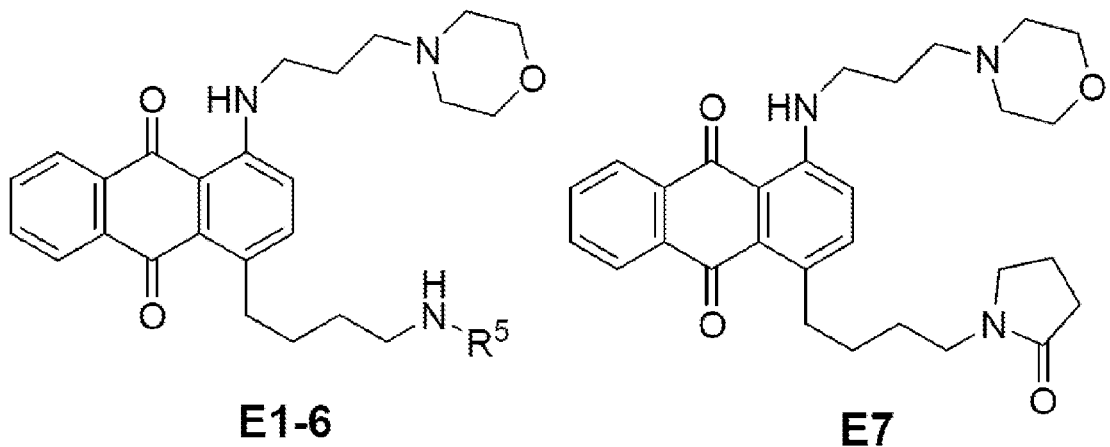
FIG. 3 illustrates the chemical structures of certain embodiments.
Figure 3:
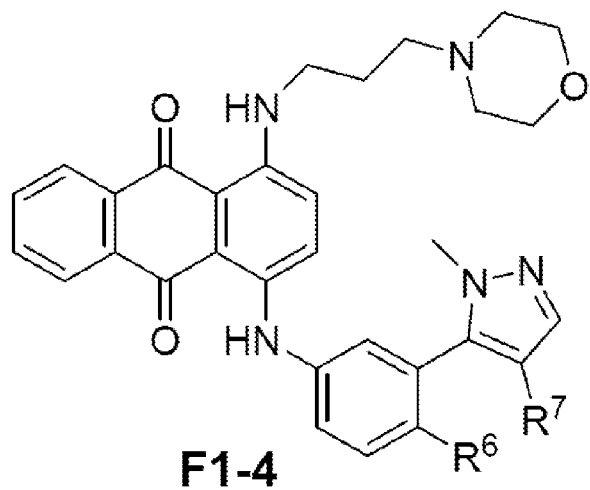

BDA-366-induced Bcl2 conformational change was also confirmed by immunofluorescence using a Bcl2/BH3-domain specific antibody. Bcl2 immunofluorescence was low or undetectable in untreated H460 cells, and was enhanced significantly in cells treated with BDA-2. However, treatment of H460 cells with BDA-366 did not significantly affect Bcl2 expression level. These findings suggest that the negative regulation of Bcl2 activity by BDA-366 occurs through conformational change and not by a change in its expression. Because treatment of H460 cells with BDA-366 resulted in mitochondrial dysfunction (i.e. reduced Mito-SOX™ red staining and cytochrome c (Cyt c) release) and apoptosis (i.e. PARP cleavage), the binding of BDA-366 to the BH4 domain may cause exposure of the Bcl2 BH3 domain, which in turn renders Bcl2 eventually able to activate Bax, leading to apoptosis. To test this possibility, a 6A7 Bax antibody that only recognizes the conformationally changed, active, form of Bax was employed. Purified Bcl2 was treated with BDA-366 in lysis buffer for 1 h. The mixture of Bcl2/BDA-2 was then incubated with purified recombinant Bax for another 2 h, followed by IP using 6A7 antibody. Results indicate that BDA-366-treated Bcl2 but not Bcl2 alone enhanced the ability of Bax to bind to 6A7 antibody (FIG. 2F, lane 4 vs. lanes 5-7), indicating that BDA-366-treated Bcl2 can induce Bax conformational change leading to Bax activation. BAM7 is a Bax activator that can directly activate Bax by binding to a Bax trigger site. Importantly, BAM7 but not BDA-366 can directly activate Bax. These findings indicate that BDA-2 is not a direct Bax activator but can induce Bcl2-dependent Bax activation.

To test whether BDA-366-induced Bcl2 conformational change increases interaction between Bcl2 and Bax in cells, co-IP experiments were performed following treatment of H460 cells with BDA-366. Results reveal that BDA-2 enhanced Bcl2/Bax interaction in association with decreased Bcl2/Bim binding suggesting that the BH3-exposed Bcl2 induced by BDA-366 may have greater ability to interact with Bax than Bim leading to activation of Bax's cell killing function via a 6A7 conformational change in cancer cells.

To further test whether the BH3 domain of Bcl2 is important for BDA-366 activation of Bax, purified recombinant WT and the BH3 deletion (ΔBH3) mutant Bcl2 proteins were incubated with purified Bax protein in the absence or presence of BDA-366, followed by IP with 6A7 antibody. Results indicate that, in the presence of BDA-366, WT but not the ΔBH3 mutant Bcl2 can activate Bax via 6A7 conformational change in a cell-free system. To test this at the cellular or mitochondrial level, WT, ΔBH3 Bcl2 mutant and empty vector (pCIneo) were transfected into H1299 cells that express undetectable levels of endogenous Bcl2 but high levels of endogenous Bax. Cells or isolated mitochondria from these cells were treated with BDA-2, followed by IP with Bcl2 BH3 or 6A7 antibody, respectively.

Results indicate that BDA-366 induced Bcl2 conformational change in association with Bax activation in cells or isolated mitochondria containing WT Bcl2 but not in cells or isolated mitochondria expressing ΔBH3 Bcl2 mutant or vector-only control. These results suggest that exposure of Bcl2 BH3 domain induced by BDA-366 is required for BDA-2 activation of Bax in cells or isolated mitochondria. To further test whether BDA-366 induces Cyt c release from mitochondria in a Bcl2 dependent fashion, mitochondria were isolated from H1299 cells expressing WT, ΔBH3 mutant Bcl2 or vector-only control. The isolated mitochondria were treated with BDA-366 (1 μM) for 30 min at 30° C. After centrifugation, Cyt c in the supernatant (i.e. Cyt c release) was analyzed by Western blot.

Results reveal that BDA-366 induced Cyt c release from the mitochondria isolated from WT Bcl2 but not from ΔBH3 and vector-only control cells. This indicates that BDA-366-induced Cyt c release occurs in a Bcl2-dependent fashion, which also requires the BH3 domain in Bcl2.

BDA-2 Induces Apoptotic Cell Death in a Bax-Dependent Manner

The BDA-366-induced conformationally changed Bcl2 (i.e. with exposed BH3 domain) can activate Bax. To further determine whether Bax is important for BDA-2 induction of apoptosis, the apoptotic effect of BDA-366 was tested on wild type (WT) and Bax knockout (Bax−/−) MEF cells. Bax deficient MEF cells were significantly resistant to BDA-366 as compared to WT MEF cells, indicating that activation of Bax by conformationally changed Bcl2 may be important for the eventual induction of apoptosis by BDA-366. BDA-366 induces calcium (Ca2+) release via inhibition of Bcl2/IP3R interaction Bcl2 has been reported to inhibit Ca2+-driven apoptosis by direction interaction with the inositol 1,4,5-trisphosphate (IP3) receptor via the BH4 domain. Disruption of BH4/IP3R association by synthetic BH4 binding peptide resulted in increased $Ca^2$+ release and apoptosis. To test whether BDA-2/BH4 binding affects the IP3R/Bcl2 interaction and Ca2+ release, H460 cells were treated with increasing concentrations of BDA-366 for 24 h. Results reveal that BDA-366 reduced Bcl2/IP3R binding in association with increased Ca2+ release. These findings may uncover an additional mechanism by which BDA-366 induces apoptosis in a BH4 binding-dependent manner.

BDA-2 Induces Autophagic Cell Death of Human Lung Cancer Cells

Bcl2 directly interacts with Beclin-1 and suppresses Beclin-1-dependent autophagy. Inhibition of Bcl2 by ABT-737 not only induces apoptosis but also autophagy. Importantly, a report indicates that removal of the BH4 domain from Bcl2 protein promotes an autophagic process that impairs tumor growth. To test whether disruption of Bcl2 BH4 by BDA-2 stimulates autophagy, H460 cells were treated with BDA-366 (1 μM) for 24 h. Increased levels of LC3-II were observed after treatment with BDA-366. To further quantify the level of autophagy, a GFP-LC3 construct was used to indicate autophagosomes. After treatment with BDA-2, GFP-LC3 redistributes from a diffuse staining pattern in the cytoplasm and nucleus to a cytoplasmic punctate structure that specifically labels pre-autophagosomal and autophagosomal membranes (i.e. GFP-LC3 vac cells). Treatment of cells with BDA-366 significantly increases the percentage of GFP-LC3vac cells as compared to DMSO control. These findings reveal that, in addition to apoptosis, BDA-366 may also stimulate autophagic cell death by inhibiting Bcl2 activity in human lung cancer cells.

BDA-366 Suppresses Lung Cancer Growth Via Induction of Apoptosis in Animal Models In order to define the appropriate doses for in vivo experimentation, the maximum tolerated dose (MTD) was determined. Nu/Nu nude mice were treated in groups of 6 per dose level with increasing doses of BDA-366 (10-50 mg/kg/d) intraperitoneally (i.p.) for up to 12 days. Doses of 40 and 50 mg/kg/d were uniformly lethal in the 6 mice within 8 or 12 days, respectively. The dose range between 10 and 30 mg/kg/d was tolerable with no death recorded for up to 12 days of daily administration. Standard single-dose MTD treatment in normal C57BL/6 mice were measured. Treatment of mice with a single dose of 300 mg/kg i.p. did not cause weight loss or other toxicities, including hematologic, liver and kidney functions. However, a single dose of 400 mg/kg resulted in death of mice in 4 days. Both ALT and AST were significantly enhanced. Pathological analysis for all organs indicated microsteatosis in the liver and atrophic white pulp in the spleen. Based on these findings, mice might die mainly from liver damage at a single 400 mg/kg dose. Thus, the single dose MTD of BDA-366 should range from 300-400 mg/kg. 10% of single dose MTD can usually be considered as the maximum therapeutic dose (30~40 mg/kg) for continuous treatment. In certain embodiments, the disclosure contemplates administration between 10 and 30 mg/kg/d to be relatively safe.

Figure 4:
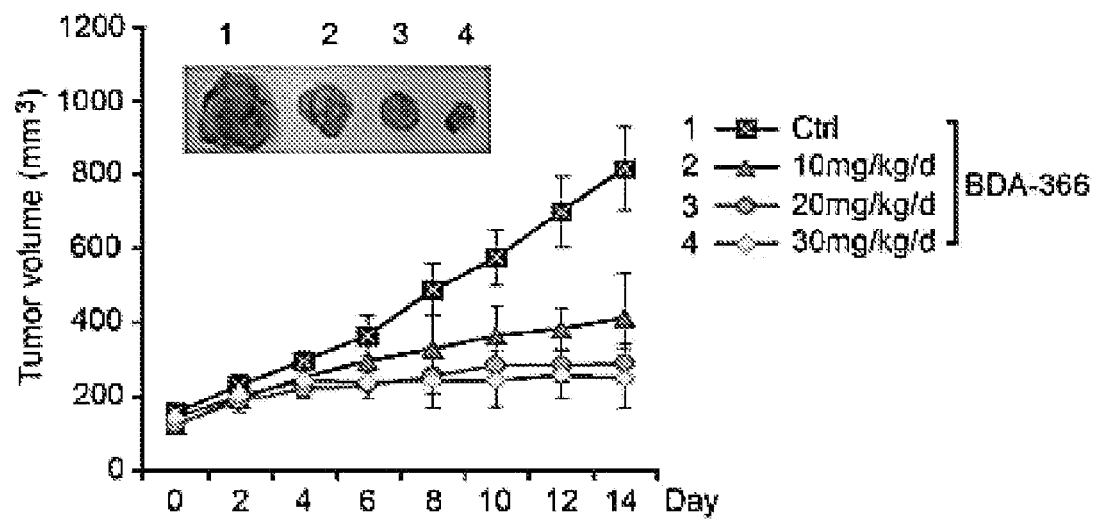
FIG. 4 shows data indicating BDA-2 (re-named as BDA-366) represses lung cancer in vivo. Nu/Nu mice with H460 lung cancer xenografts were treated with increasing doses of BDA-366 (0, 10, 20 and 30 mg/kg/d) for 14 days. Each group included 8 mice. Tumor volume was measured once every 2 days. After 14 days, the mice were sacrificed and the tumors were removed and analyzed.

To test the potency of BDA-366 in vivo, lung cancer xenografts derived from H460 cells were treated with increasing doses (0, 10, 20, 30 mg/kg/d) of BDA-366 via i.p. for 14 days. Results show that treatment of mice with BDA-366 resulted in a dose-dependent repression of lung cancer in vivo (FIG. 4). To assess whether BDA-366 induced suppression of tumor growth via apoptosis in vivo, representative samples from harvested tumor tissues were analyzed by immunohistochemistry (IHC) for active caspase 3 or TUNEL assat. A dose-dependent apoptosis induction was observed in tumor tissues after BDA-366 treatment (FIG. 4C). Importantly, doses of 10-30 mg/kg/d not only potently suppressed tumor growth but were also well tolerated without significant toxicity to mice. Weight loss was observed in mice treated with the dose of 30 mg/kg but there were no decreases in neutrophils, lymphocytes, red blood cells (RBC) and platelets (PLT) in blood. Tests of kidney (BUN) and liver (ALT and AST) function were in the normal range. Histopathology of harvested normal tissues (heart, liver, lung, brain, spleen, kidney, intestine, etc.) revealed no evidence of normal tissue toxicities after treatment with doses of 10-30 mg/kg/d.

Figure 5:
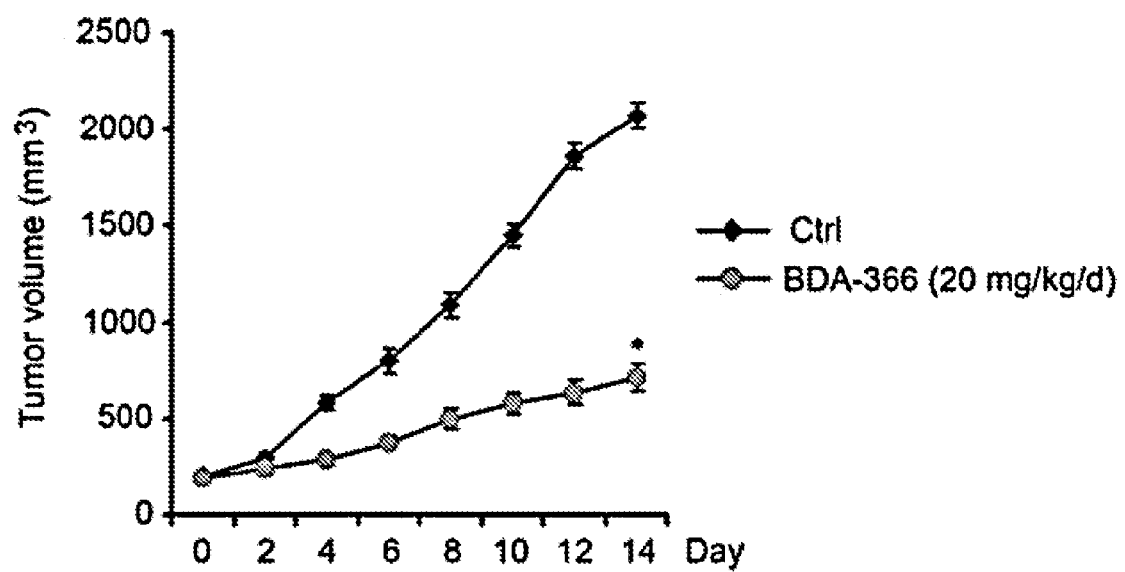
FIG. 5 shows data indicating BDA-366 represses tumor growth in xenografts derived from SCLC patient. Mice carrying xenografts derived from a patient with refractory SCLC were treated with BDA-366 (20 mg/kg/d) via i.p. for 2 weeks.
Figure 6:
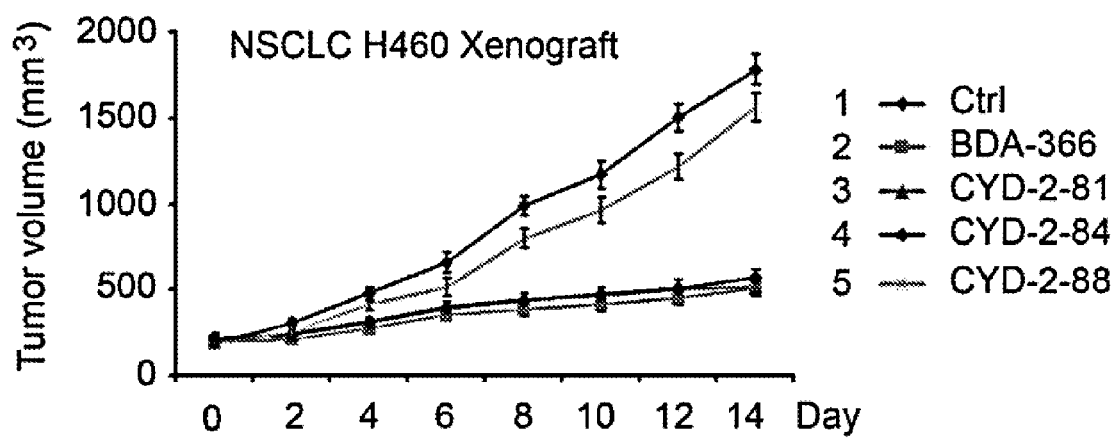
FIG. 6 shows tumor volume data on certain embodiments of this disclosure. NSCLC H460 xenografts mice were treated with 20 mg/kg of Bcl2 BH4 antagonist BDA-366 or its analogs (CYD-2-81, CYD-2-84 and CYD-2-88) via. i.p. for two weeks.

In addition to NSCLC cell lines, BDA-366 also efficiently suppressed growth of SCLC cell lines. To evaluate the anti-tumor activity of BDA-2 against SCLC in vivo, patient-derived xenografts (PDX) were established without intervening in vitro culture, which are expected to better recapitulate the SCLC tumor setting. The potency of BDA-366 (20 mg/kg/d) was tested by administering for 2 weeks in a PDX obtained from a patient with refractory SCLC. BDA-366 potently suppressed the growth of the SCLC PDX, which occurred through apoptosis in tumor tissues (FIG. 5). These findings indicate that BDA-2 may be effective in human patients with SCLC where there are currently limited treatment options.

BDA-366 Induces Bcl2 Conformational Change in Tumor Tissues

Figure 7:
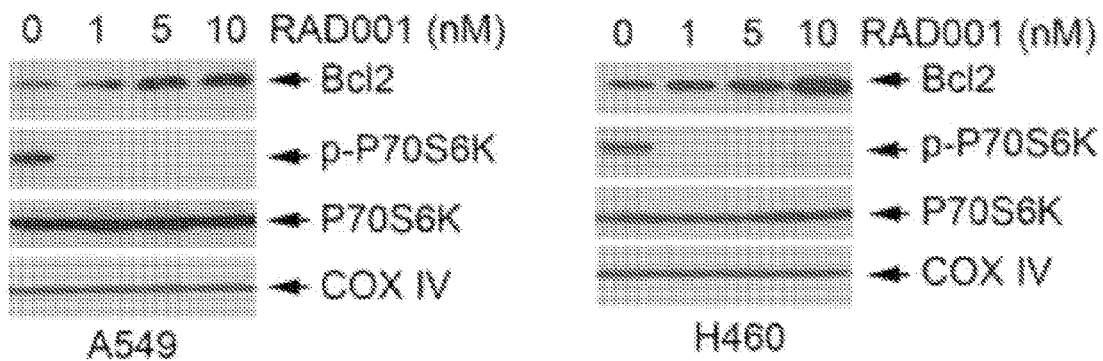
FIG. 7 shows data indicating treatment of lung cancer cells or patients with RAD001 up-regulates Bcl2. A549 or H460 cells were treated with increasing concentrations of RAD001 for 24 h. Bcl2 and p-P70S6K were analyzed by Western blot.

Quantum dot-based immunohistofluorescence (QD-IHF) technology has recently been developed as a valuable tool for simultaneous and concurrent immunostaining of multiple biomarkers in formalin-fixed paraffin-embedded (FFPE) tissues, thereby allowing for quantification of several biomarkers simultaneously on the same tissue slide. To determine whether BDA-366 induces Bcl2 conformation change by exposure of its BH3 domain in tumor tissues and whether the BH3 domain-exposed Bcl2 activates Bax, conformational changes in both Bcl2 and Bax were simultaneously analyzed by QD-IHF on the same tissue slide. The antibody 6A7 can selectively recognize Bax after the conformational change associated with membrane insertion that occurs in apoptotic cells. QD images showed that treatment of H460 xenograft mice with BDA-366 for 14 days resulted in a dose-dependent exposure of the Bcl2 BH3 domain in tumor tissues. Intriguingly, BDA-366-induced Bcl2 conformational change was associated with an increased level of 6A7 binding to Bax (i.e. an increase in the level of the active form of Bax), suggesting that the BH3-exposed Bcl2 may activate Bax leading to apoptosis in tumor tissues. There were no significant changes in total Bcl2 and Bax levels in tumor tissues after BDA-366 treatment.

mTOR Inhibition Up-regulates Bcl2 in Lung Cancer Cell Lines and in Tumor Tissues from Patients with NSCLC Rapamycin and its derivative RAD001 (i.e. everolimus) are potent allosteric inhibitors of mTOR. RAD001 is well tolerated but shows limited antitumor activity in patients with lung cancer. Previous reports indicate that expression of Bcl2 is associated with resistance of cancer cells to mTOR inhibitors. To further test whether mTOR inhibition regulates Bcl2 expression, A549 and H460 cells were treated with increasing concentrations of RAD001 for 24 hr. Inhibition of mTOR by RAD001 resulted in up-regulation of Bcl2 in a dose-dependent manner in both A549 and H460 lung cancer cells (FIG. 7A).

To test whether a similar effect of RAD001 on Bcl2 expression occurs in patients Bcl2 expression was analyzed by IHC in baseline and post-treatment tissue samples obtained from 10 NSCLC patients treated with RAD001 (5 or 10 mg/day) for 28 days as part of a neoadjuvant clinical study of everolimus in patients with resectable NSCLC. There was increased expression of Bcl2 in post-treatment tumor tissues compared to baseline samples. These findings suggest that up-regulation of Bcl2 by mTOR inhibition may negatively affect the sensitivity of lung cancer to mTOR inhibitor. Thus, inhibition of Bcl2 may enhance the potency of mTOR inhibitor against lung cancer.

Figure 8:
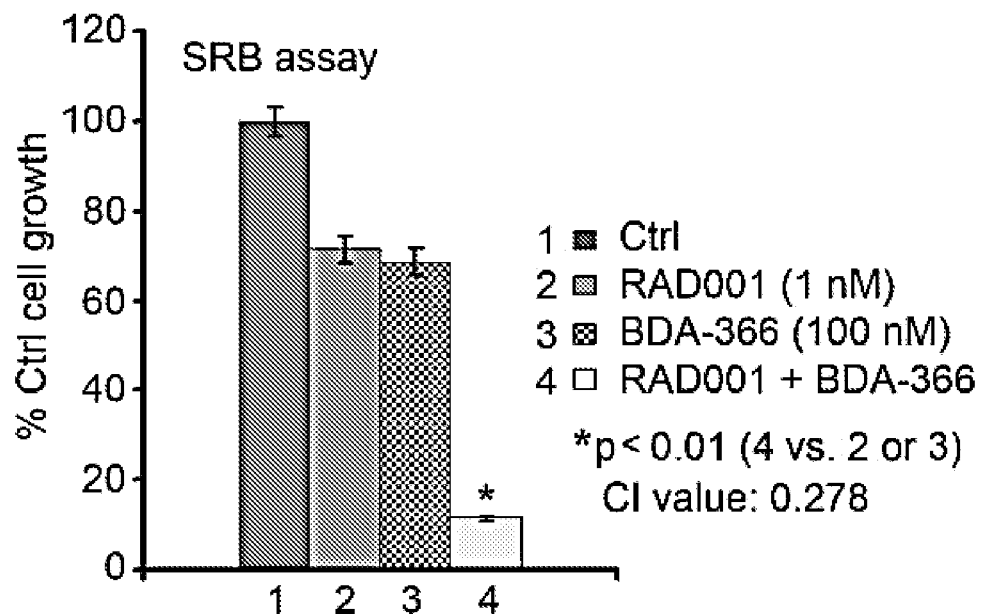
FIG. 8 shows data indicating BDA-366 synergizes with RAD001 in suppression of human lung cancer cell growth. H460 cells were treated with RAD001 (1 nM) or BDA-366 (100 nM) alone or in combination for 72 hr. Cell growth was analyzed by sulforhodamine B (SRB) colorimetric assay. Combination index (CI) value for evaluating synergy of RAD001 and BDA-366 was calculated using the CompuSyn software.

BDA-366 Synergizes with mTOR Inhibitor in Suppression of Lung Cancer In Vitro and In Vivo To test whether combined Bcl2 and mTOR inhibition shows synergistic activity against lung cancer cells, H460 cells were treated with BDA-366 (100 nM), RAD001 (1 nM) or the combination. SRB assay showed that either RAD001 or BDA-366 alone partially inhibited lung cancer cell growth. Intriguingly, the combination of RAD001 and BDA-366 resulted in significantly more growth inhibition (FIG. 8), indicating that combined Bcl2 and mTOR inhibition has greater activity than either single agent alone in inhibiting lung cancer cell growth. To more accurately analyze the degree of synergy between RAD001 and BDA-366, a combination index (CI) value was calculated. The CI value was less than 0.3 (i.e. 0.278), indicating that RAD001 and BDA-366 exhibit strong synergistic growth inhibition of lung cancer cells.

Figure 9:
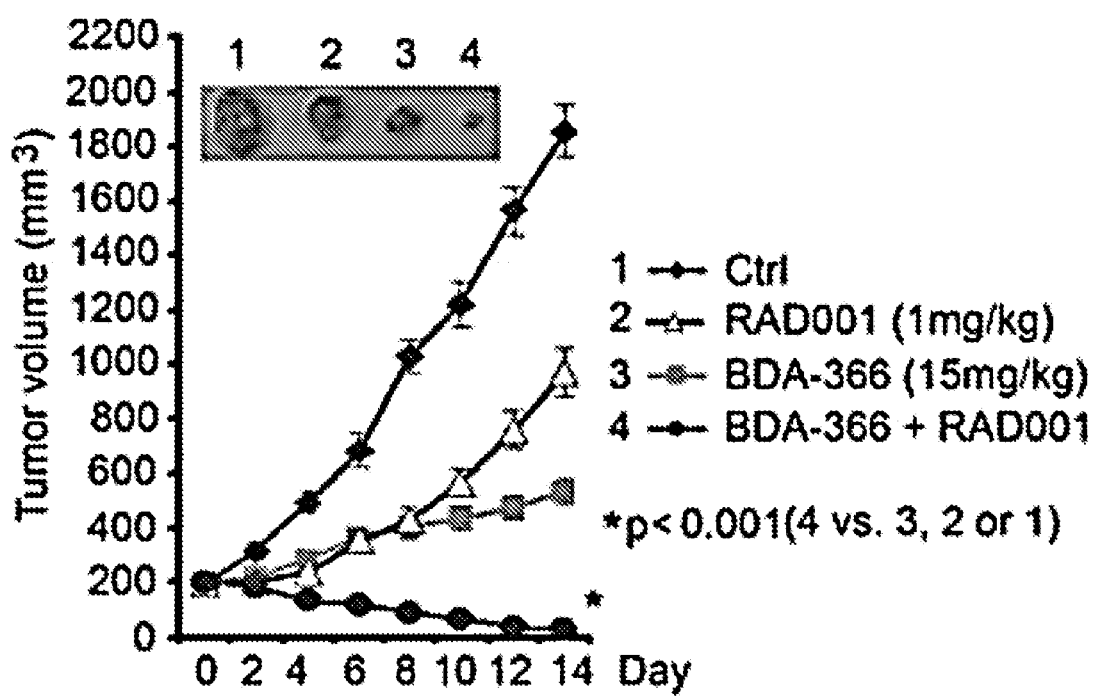
FIG. 9 shows a combination of BDA-366 and RAD001 synergistically represses lung cancer in vivo. Nu/Nu mice with H460 lung cancer xenografts were treated with BDA-366, RAD001 or their combination by i.p. for 14 days.
Figure 10:
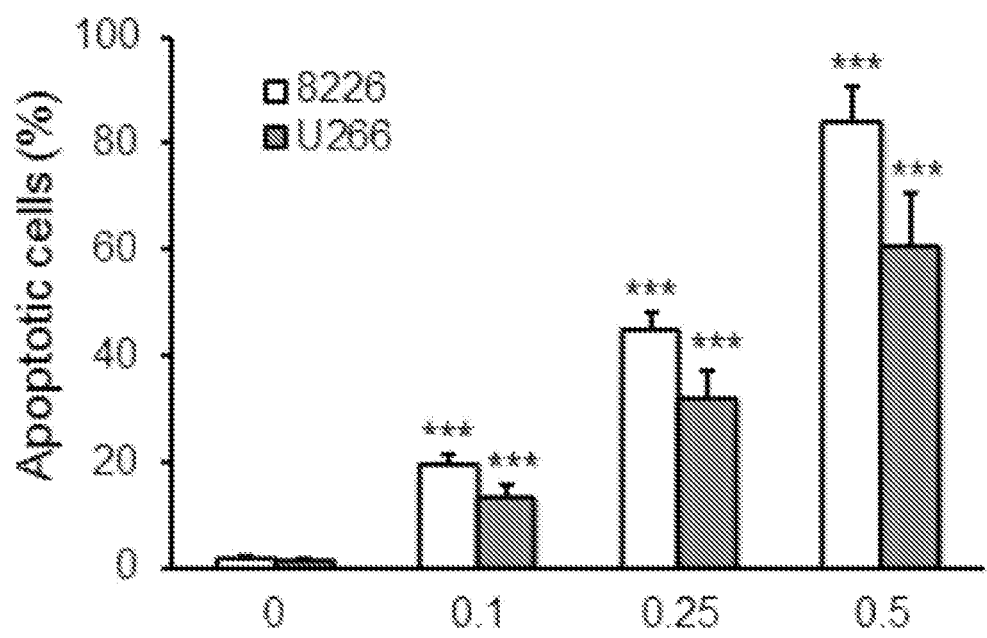
FIG. 10 shows data when human multiple myeloma cell lines 8226 and U266 (106 cells/ml) were treated with BDA2 at different concentration (0, 0.1, 0.25, 0.50 µM) for 48 hr. Cells were then stained with Annexin V for FACS analysis. Apoptotic cell death is presented as percentage of Annexin V positive cells. The number of live cells in the treatments was counted under a microscope with typan blue staining.

To test whether co-targeting Bcl2 and mTOR also synergistically represses lung cancer in vivo, mice with NSCLC (i.e. H460) xenografts were treated with RAD001 (1 mg/kg/d), BDA-366 (15 mg/kg/d) or the combination for 14 days. Intriguingly, the combination of BDA-366 and RAD001 exhibited a significantly greater efficacy than BDA-366 or RAD001 alone in suppressing lung tumor growth in vivo (FIG. 9), leading to sustained tumor repression.

3. The method of claim 1, wherein the mTOR inhibitor has the following formula,

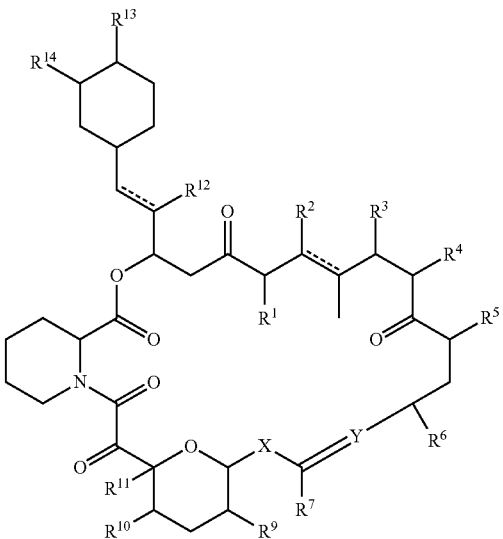

or salts thereof wherein,
the dotted lines each individually represent a single or double bond;
Y is the bridging group =CH—CH=CH—CH=CH—;
X is —(CHR$^8$)$_n$—;
n is 1 or 2
$R^1$, $R^2$, $R^3$, $R^4$, $R^5$, $R^7$, $R^8$, $R^9$, $R^{10}$, $R^{11}$, $R^{12}$, $R_{13}$, and $R^{14}$ are each the same or different, individually and independently at each occurrence, hydrogen, alkyl, alkenyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, phosphinyl, carbocyclyl, aryl, or heterocyclyl, wherein each $R^1$, $R^2$, $R^3$, $R^4$, $R^5$, $R^7$, $R^8$, $R^9$, $R^{10}$, $R^{11}$, $R^{12}$, $R_{13}$, and $R^{14}$ are optionally substituted with one or more, the same or different, $R^{20}$;
$R^{20}$ is alkyl, halogen, nitro, cyano, hydroxy, amino, mercapto, formyl, carboxy, alkanoyl, carbamoyl, alkoxy,

The invention claimed is:

1. A method of treating lung cancer comprising administering an effective amount of an mTOR inhibitor in combination with 1-((3-(diethylamino)-2-hydroxypropyl)amino)-4-((oxiran-2-ylmethyl)amino)anthracene-9,10-dione or salt thereof to a subject diagnosed with lung cancer.

2. The method of claim 1, wherein the mTOR inhibitor is sirolimus, everolimus, ridaforolimus, or temsirolimus.

alkylthio, alkylamino, (alkyl)$_2$amino, alkylsulfinyl, alkyl sulfonyl, arylsulfonyl, phosphinyl, carbocyclyl, aryl, or heterocyclyl, wherein $R^{20}$ is optionally substituted with one or more, the same or different, $R^{21}$; and
$R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

* * * * *

SEQUENCE LISTING

<160> NUMBER OF SEQ ID NOS: 1

<210> SEQ ID NO 1
<211> LENGTH: 10
<212> TYPE: PRT
<213> ORGANISM: Homo sapiens

<400> SEQUENCE: 1

Gln Asp Cys Met Trp Ser Gly Phe Ser Ala
1               5                   10